(12) United States Patent
Chan et al.

(10) Patent No.: US 8,497,630 B2
(45) Date of Patent: Jul. 30, 2013

(54) METHODS OF ANALYZING PEPTIDE MIXTURES

(75) Inventors: Hardy Chan, San Mateo, CA (US); Jentaie Shiea, Kaohsiung (TW); Yi-Tzu Cho, Kaohsiung (TW); Chi-Hsien Lin, Tainan County (TW)

(73) Assignee: Scinopharm Taiwan Ltd., Tainan (TW)

( * ) Notice: Subject to any disclaimer, the term of this patent is extended or adjusted under 35 U.S.C. 154(b) by 389 days.

(21) Appl. No.: 12/775,747

(22) Filed: May 7, 2010

(65) Prior Publication Data

US 2010/0285513 A1 Nov. 11, 2010

Related U.S. Application Data

(60) Provisional application No. 61/176,579, filed on May 8, 2009.

(51) Int. Cl.
*H01J 17/26* (2012.01)

(52) U.S. Cl.
USPC .................................. 313/564; 435/4; 435/23

(58) Field of Classification Search
USPC ........................................ 313/564; 435/4, 23
See application file for complete search history.

(56) References Cited

U.S. PATENT DOCUMENTS

2006/0172429 A1  8/2006  Nilsson et al.

FOREIGN PATENT DOCUMENTS

WO  WO 2007/127977  11/2007

OTHER PUBLICATIONS

Jeng et al. "Using high-concentration trypsin-immobilized magnetic nanoparticles for rapid in situ protein digestion at elevated temperature", Rapid Communications in Mass Spectrometry, 2007, 21:3060-3068.*

Knierman et al. "Peptide fingerprints after partial acid hydrolysis: analysis by matrix-assisted laser desorption/ionization mass spectrometry", Rapid Communications in Mass Spectrometry, 1994, 8:1007-1010.*

Kurogochi et al. "Structural characterization of N-glycopeptides by matrix-dependent selective fragmentation of MALDI-TOF/TOF tandem mass spectrometry", Anal. Chem., 2004, 76:6097-6101.*

On et al., Solvent and acidity effects on the UV-visible spectra and protonation-deprotonation of free-base octaethylcorrole. Journal of Prophyrins and Pthalocyanines (2008) vol. 12, No. 1 p. 1-10.

International Search Report dated Jul. 19, 2010.

* cited by examiner

*Primary Examiner* — Bin Shen
(74) *Attorney, Agent, or Firm* — VLP Law Group LLP; Enshan Hong; Kent H. Cheng

(57) ABSTRACT

The present invention provides for a method of characterizing and classifying a sample of peptide or polypeptide mixtures or a biomolecule comprising a polypeptide component by using mass spectrometry and statistic methods for analyzing the mass spectrometry results.

13 Claims, 55 Drawing Sheets

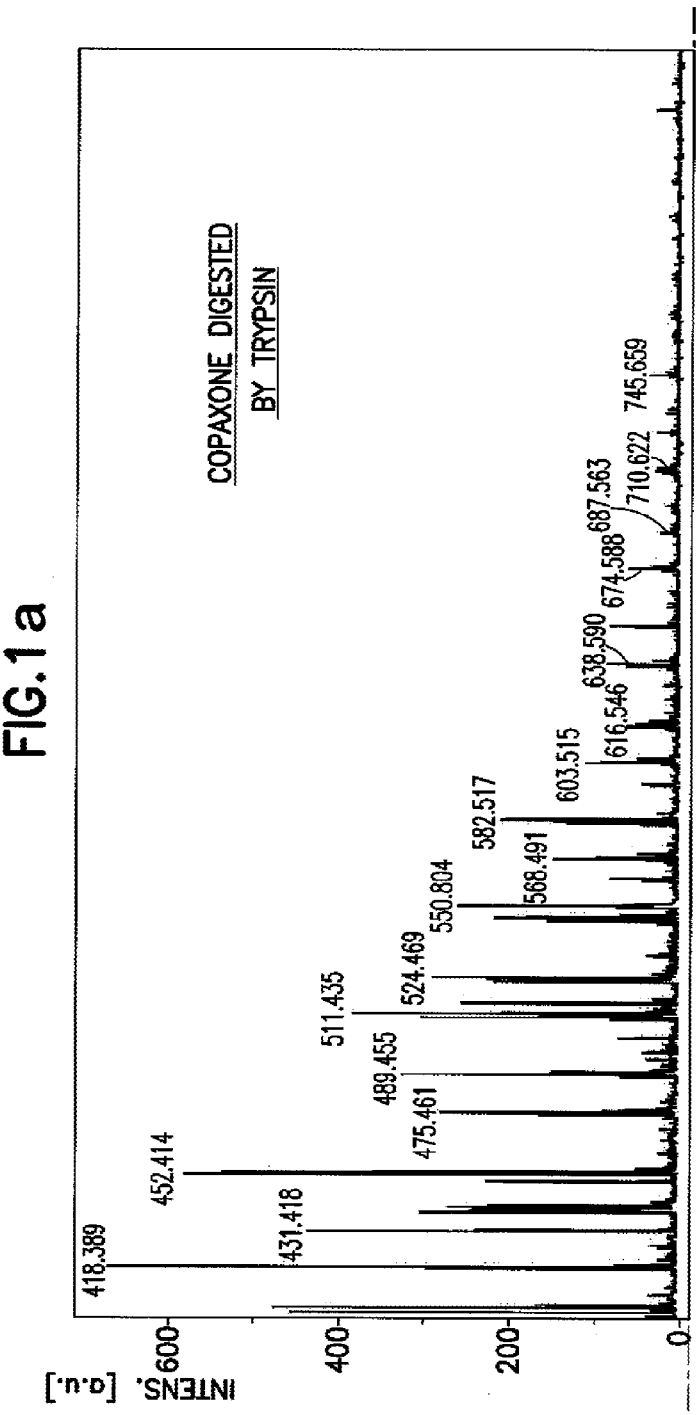

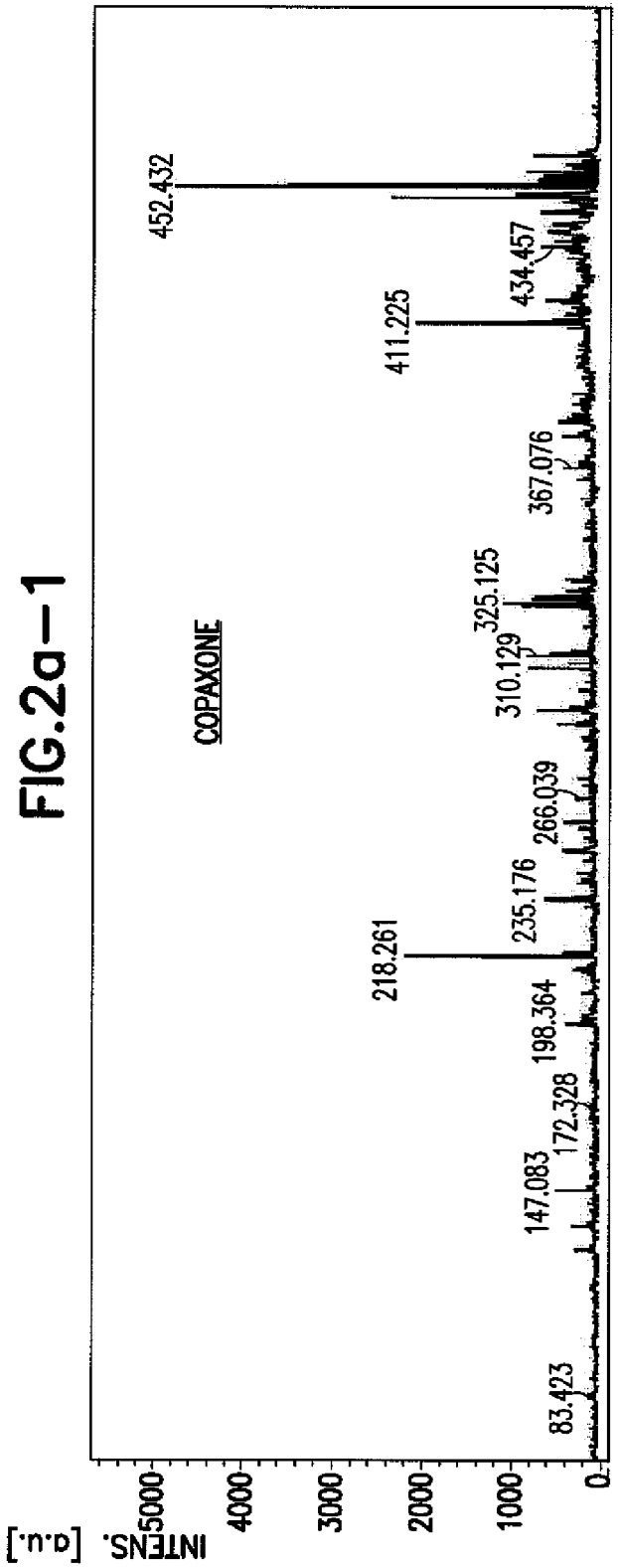

| Ion | Y | A | A | K | Tyr | Ala | Ala | Lys |
|---|---|---|---|---|---|---|---|---|
| | Y | A | A | K | 1 | 2 | 3 | 4 |
| a | Y | A | A | K | 136.076 | 207.113 | 278.150 | 406.245 |
| b | Y | A | A | K | 164.071 | 235.108 | 306.145 | 434.240 |
| a-17 | Y | A | A | K | 119.049 | 190.086 | 261.123 | 389.218 |
| a-18 | Y | A | A | K | 118.065 | 189.102 | 260.139 | 388.234 |
| b-17 | Y | A | A | K | 147.044 | 218.081 | 289.118 | 417.213 |
| b-18 | Y | A | A | K | 146.060 | 217.097 | 288.134 | 416.229 |
| b+18 | Y | A | A | K | 182.081 | 253.118 | 324.155 | 452.250 |
| y | Y | A | A | K | 147.113 | 218.150 | 289.187 | 452.250 |
| y-17 | Y | A | A | K | 130.110 | 201.147 | 272.184 | 435.248 |
| i | Y | A | A | K | 136.076 | 44.049 | 44.049 | 101.107 |
| | 4 | 3 | 2 | 1 | Lys | Ala | Ala | Tyr |

| FIG.2b-1A |
|---|
| FIG.2b-1B |

| Ion | Y | A | A | K | Tyr | Ala | Ala | Lys |
|---|---|---|---|---|---|---|---|---|
| | | | | | 1 | 2 | 3 | 4 |
| a | Y | A | A | K | 136.076 | 207.113 | 278.150 | 406.245 |
| a-17 | Y | A | A | K | 119.049 | 190.086 | 261.123 | 389.218 |
| a-18 | Y | A | A | K | 118.065 | 189.102 | 260.139 | 388.234 |
| b | Y | A | A | K | 164.071 | 235.108 | 306.145 | 434.240 |
| b-17 | Y | A | A | K | 147.044 | 218.081 | 289.118 | 417.213 |
| b-18 | Y | A | A | K | 146.060 | 217.097 | 288.134 | 416.229 |
| b+18 | Y | A | A | K | 182.081 | 253.118 | 324.155 | 452.250 |
| c | Y | A | A | K | 181.097 | 252.134 | 323.171 | 451.266 |
| x | Y | A | A | K | 173.092 | 244.129 | 315.166 | 478.230 |
| y | Y | A | A | K | 147.113 | 218.150 | 289.187 | 452.250 |
| z | Y | A | A | K | 130.086 | 201.123 | 272.160 | 435.224 |
| i | Y | A | A | K | 136.076 | 44.049 | 44.049 | 101.107 |
| | 4 | 3 | 2 | 1 | Lys | Ala | Ala | Tyr |

| Ion | E | A | Y | K | Glu 1 | Ala 2 | Tyr 3 | Lys 4 |
|---|---|---|---|---|---|---|---|---|
| a | 1 | 2 | 3 | 4 | 102.055 | 173.092 | 336.155 | 464.250 |
| a-17 | E | A | Y | K | 85.028 | 156.066 | 319.129 | 447.224 |
| a-18 | E | A | Y | K | 84.044 | 155.082 | 318.145 | 446.240 |
| b | E | A | Y | K | 130.050 | 201.087 | 364.150 | 492.245 |
| b-17 | E | A | Y | K | 113.023 | 184.060 | 347.124 | 475.219 |
| b-18 | E | A | Y | K | 112.039 | 183.076 | 346.140 | 474.235 |
| b+18 | E | A | Y | K | 148.060 | 219.098 | 382.161 | 510.256 |
| c | E | A | Y | K | 147.076 | 218.114 | 381.177 | 509.272 |
| x | E | A | Y | K | 173.092 | 336.155 | 407.193 | 536.235 |
| y | E | A | Y | K | 147.113 | 310.176 | 381.213 | 510.256 |
| z | E | A | Y | K | 130.086 | 293.150 | 364.187 | 493.229 |
| i | | | | | 102.055 | 44.049 | 136.075 | 101.107 |
| | 4 | 3 | 2 | 1 | Lys | Tyr | Ala | Glu |

| FIG.3b-1A |
|---|
| FIG.3b-1B |

| Ion | E | A | Y | K | Glu | Ala | Ala | Lys |
|---|---|---|---|---|---|---|---|---|
| | 1 | 2 | 3 | 4 | 1 | 2 | 3 | 4 |
| a | E | A | Y | K | 102.055 | 173.092 | 336.155 | 464.250 |
| b | E | A | Y | K | 130.050 | 201.087 | 364.150 | 492.245 |
| a-17 | E | A | Y | K | 85.028 | 156.066 | 319.129 | 447.224 |
| a-18 | E | A | Y | K | 84.044 | 155.082 | 318.145 | 446.240 |
| b-17 | E | A | Y | K | 113.023 | 184.060 | 347.124 | 475.219 |
| b-18 | E | A | Y | K | 112.039 | 183.076 | 346.140 | 474.235 |
| b+18 | E | A | Y | K | 148.060 | 219.098 | 382.161 | 510.256 |
| y | E | A | Y | K | 147.113 | 310.176 | 381.213 | 510.256 |
| y-17 | E | A | Y | K | 130.110 | 293.173 | 364.211 | 493.253 |
| i | E | A | Y | K | 102.055 | 44.049 | 136.075 | 101.107 |
| | 4 | 3 | 2 | 1 | Lys | Tyr | Ala | Glu |

FIG.3b-2B

| FIG.3b-2A |
|---|
| FIG.3b-2B |

FIG.3b-2

| Ion | Y | E | A | K | Tyr | Glu | Ala | Lys |
|---|---|---|---|---|---|---|---|---|
|  | 1 | 2 | 3 | 4 | 1 | 2 | 3 | 4 |
| a | Y | E | A | K | 136.076 | 265.118 | 336.155 | 464.250 |
| a-17 | Y | E | A | K | 119.049 | 248.092 | 319.129 | 447.224 |
| a-18 | Y | E | A | K | 118.065 | 247.108 | 318.145 | 446.240 |
| b | Y | E | A | K | 164.071 | 293.113 | 364.150 | 492.245 |
| b-17 | Y | E | A | K | 147.044 | 276.087 | 347.124 | 475.219 |
| b-18 | Y | E | A | K | 146.060 | 275.103 | 346.140 | 474.235 |
| b+18 | Y | E | A | K | 182.081 | 311.124 | 382.161 | 510.256 |
| c | Y | E | A | K | 181.097 | 310.140 | 381.177 | 509.272 |
| x | Y | E | A | K | 173.092 | 244.129 | 373.172 | 536.235 |
| y | Y | E | A | K | 147.113 | 218.150 | 347.193 | 510.256 |
| z | Y | E | A | K | 130.086 | 201.123 | 330.166 | 493.229 |
| i | Y | E | A | K | 136.076 | 102.054 | 44.049 | 101.107 |
|  | 4 | 3 | 2 | 1 | Lys | Ala | Glu | Tyr |

| Ion | Y | E | A | K |  | Tyr | Glu | Ala | Lys |
|---|---|---|---|---|---|---|---|---|---|
|  | 1 | 2 | 3 | 4 |  | 1 | 2 | 3 | 4 |
| a | Y | E | A | K |  | 136.076 | 265.118 | 336.155 | 464.250 |
| b | Y | E | A | K |  | 164.071 | 293.113 | 364.150 | 492.245 |
| a-17 | Y | E | A | K |  | 119.049 | 248.092 | 319.129 | 447.224 |
| a-18 | Y | E | A | K |  | 118.065 | 247.108 | 318.145 | 446.240 |
| b-17 | Y | E | A | K |  | 147.044 | 276.087 | 347.124 | 475.219 |
| b-18 | Y | E | A | K |  | 146.060 | 275.103 | 346.140 | 474.235 |
| b+18 | Y | E | A | K |  | 182.081 | 311.124 | 382.161 | 510.256 |
| y | Y | E | A | K |  | 147.113 | 218.150 | 347.193 | 510.256 |
| y-17 | Y | E | A | K |  | 130.110 | 201.147 | 330.190 | 493.253 |
| i | Y | E | A | K |  | 136.076 | 102.054 | 44.049 | 101.107 |
|  | 4 | 3 | 2 | 1 |  | Lys | Ala | Tyr | Tyr |

| Ion | K | A | E | K | K | | Lys | 1 | Ala | 2 | Glu | 3 | Lys | 4 | Lys | 5 |
|---|---|---|---|---|---|---|---|---|---|---|---|---|---|---|---|---|
| a | 1 | 2 | 3 | 4 | 5 | | 101.107 | | 172.144 | | 301.187 | | 429.282 | | 557.377 | |
| a-17 | K | A | E | K | K | | 84.081 | | 155.118 | | 284.160 | | 412.255 | | 540.350 | |
| a-18 | K | A | E | K | K | | 83.097 | | 154.134 | | 283.176 | | 411.271 | | 539.366 | |
| b | K | A | E | K | K | | 129.102 | | 200.139 | | 329.182 | | 457.277 | | 585.372 | |
| b-17 | K | A | E | K | K | | 112.076 | | 183.113 | | 312.155 | | 440.250 | | 568.345 | |
| b-18 | K | A | E | K | K | | 111.092 | | 182.129 | | 311.171 | | 439.266 | | 567.361 | |
| b+18 | K | A | E | K | K | | 147.113 | | 218.150 | | 347.193 | | 475.287 | | 603.382 | |
| c | K | A | E | K | K | | 146.129 | | 217.166 | | 346.208 | | 474.303 | | 602.398 | |
| x | K | A | E | K | K | | 173.092 | | 301.187 | | 430.230 | | 501.267 | | 629.362 | |
| y | K | A | E | K | K | | 147.113 | | 275.208 | | 404.250 | | 475.287 | | 603.382 | |
| z | K | A | E | K | K | | 130.086 | | 258.181 | | 387.224 | | 458.261 | | 586.356 | |
| i | K | A | E | K | K | | 101.107 | | 44.049 | | 102.054 | | 101.107 | | 101.107 | |
| | 5 | 4 | 3 | 2 | 1 | | Lys | | Lys | | Glu | | Ala | | Lys | |

| Ion | | | | | | Lys 1 | Ala 2 | Glu 3 | Lys 4 | Lys 5 |
|---|---|---|---|---|---|---|---|---|---|---|
| a | K 1 | A 2 | E 3 | K 4 | K 5 | 101.107 | 172.144 | 301.187 | 429.282 | 557.377 |
| a-17 | K | A | E | K | K | 84.081 | 155.118 | 284.160 | 412.255 | 540.350 |
| a-18 | K | A | E | K | K | 83.097 | 154.134 | 283.176 | 411.271 | 539.366 |
| b | K | A | E | K | K | 129.102 | 200.139 | 329.182 | 457.277 | 585.372 |
| b-17 | K | A | E | K | K | 112.076 | 183.113 | 312.155 | 440.250 | 568.345 |
| b-18 | K | A | E | K | K | 111.092 | 182.129 | 311.171 | 439.266 | 567.361 |
| b+18 | K | A | E | K | K | 147.113 | 218.150 | 347.193 | 475.287 | 603.382 |
| c | K | A | E | K | K | 146.129 | 217.166 | 346.208 | 474.303 | 602.398 |
| x | K | A | E | K | K | 173.092 | 301.187 | 430.230 | 501.267 | 629.362 |
| y | K | A | E | K | K | 147.113 | 275.208 | 404.250 | 475.287 | 603.382 |
| z | K | A | E | K | K | 130.086 | 258.181 | 387.224 | 458.261 | 586.356 |
| i | K | A | E | K | K | 101.107 | 44.049 | 102.054 | 101.107 | 101.107 |
| | 5 | 4 | 3 | 2 | 1 | Lys | Ala | Glu | Ala | Lys |

| Ion | K 1 | A 2 | E 3 | K 4 | K 5 | Lys 1 | Ala 2 | Glu 3 | Lys 4 | Lys 5 |
|---|---|---|---|---|---|---|---|---|---|---|
| a | K | A | E | K | K | 101.107 | 172.144 | 301.187 | 464.250 | 592.345 |
| a-17 | K | A | E | K | K | 84.081 | 155.118 | 284.160 | 447.224 | 575.319 |
| a-18 | K | A | E | K | K | 83.097 | 154.134 | 283.176 | 446.240 | 574.335 |
| b | K | A | E | K | K | 129.102 | 200.139 | 329.182 | 492.245 | 620.340 |
| b-17 | K | A | E | K | K | 112.076 | 183.113 | 312.155 | 475.219 | 603.314 |
| b-18 | K | A | E | K | K | 111.092 | 182.129 | 311.171 | 474.235 | 602.330 |
| b+18 | K | A | E | K | K | 147.113 | 218.150 | 347.193 | 510.256 | 638.351 |
| c | K | A | E | K | K | 146.129 | 217.166 | 346.208 | 509.272 | 637.367 |
| x | K | A | E | K | K | 173.092 | 336.155 | 465.198 | 536.235 | 664.330 |
| y | K | A | E | K | K | 147.113 | 310.176 | 439.219 | 510.256 | 638.351 |
| z | K | A | E | K | K | 130.086 | 293.150 | 422.192 | 493.229 | 621.324 |
| i | K | A | E | K | K | 101.107 | 44.049 | 102.054 | 136.075 | 101.107 |
|  | 5 | 4 | 3 | 2 | 1 | Lys | Tyr | Glu | Ala | Lys |

| Ion | K 1 | A 2 | E 3 | Y 4 | K 5 | Lys 1 | Ala 2 | Glu 3 | Lys 4 | Lys 5 |
|---|---|---|---|---|---|---|---|---|---|---|
| a | K | A | E | Y | K | 101.107 | 172.144 | 301.187 | 464.250 | 592.345 |
| a-17 | K | A | E | Y | K | 84.081 | 155.118 | 284.160 | 447.224 | 575.319 |
| a-18 | K | A | E | Y | K | 83.097 | 154.134 | 283.176 | 446.240 | 574.335 |
| b | K | A | E | Y | K | 129.102 | 200.139 | 329.182 | 492.245 | 620.340 |
| b-17 | K | A | E | Y | K | 112.076 | 183.113 | 312.155 | 475.219 | 603.314 |
| b-18 | K | A | E | Y | K | 111.092 | 182.129 | 311.171 | 474.235 | 602.330 |
| b+18 | K | A | E | Y | K | 147.113 | 218.150 | 347.193 | 510.256 | 638.351 |
| c | K | A | E | Y | K | 146.129 | 217.166 | 346.208 | 509.272 | 637.367 |
| x | K | A | E | Y | K | 173.092 | 336.155 | 465.198 | 536.235 | 664.330 |
| y | K | A | E | YY | K | 147.113 | 310.176 | 439.219 | 510.256 | 638.351 |
| z | K | A | E | Y | K | 130.086 | 293.150 | 422.192 | 493.229 | 621.324 |
| i | K | A | E | Y | K | 101.107 | 44.049 | 102.054 | 136.075 | 101.107 |
|   | 5 | 4 | 3 | 2 | 1 | Lys | Tyr | Glu | Ala | Lys |

FIG.5b-2B

| FIG.5b-2A | FIG.5b-2B | FIG.5b-2 |

| Ion | K | A | E | A | K | K | Lys | Ala | Glu | Ala | Lys | Lys |
|---|---|---|---|---|---|---|---|---|---|---|---|---|
| | 1 | 2 | 3 | 4 | 5 | 6 | 1 | 2 | 3 | 4 | 5 | 6 |
| a | K | A | E | A | K | K | 101.107 | 172.144 | 301.187 | 372.224 | 500.319 | 628.414 |
| a-17 | K | A | E | A | K | K | 84.081 | 155.118 | 284.160 | 355.198 | 483.293 | 611.388 |
| a-18 | K | A | E | A | K | K | 83.097 | 154.134 | 283.176 | 354.214 | 482.309 | 610.404 |
| b | K | A | E | A | K | K | 129.102 | 200.139 | 329.182 | 400.219 | 528.314 | 656.409 |
| b-17 | K | A | E | A | K | K | 112.076 | 183.113 | 312.155 | 383.193 | 511.287 | 639.382 |
| b-18 | K | A | E | A | K | K | 111.092 | 182.129 | 311.171 | 382.208 | 510.303 | 638.398 |
| b+18 | K | A | E | A | K | K | 147.113 | 218.150 | 347.193 | 418.230 | 546.325 | 674.420 |
| c | K | A | E | A | K | K | 146.129 | 217.166 | 346.208 | 417.246 | 545.341 | 673.436 |
| x | K | A | E | A | K | K | 173.092 | 301.187 | 372.224 | 501.267 | 572.304 | 700.399 |
| y | K | A | E | A | K | K | 147.113 | 275.208 | 346.245 | 475.287 | 546.325 | 674.420 |
| z | K | A | E | A | K | K | 130.086 | 258.181 | 329.218 | 458.261 | 529.298 | 657.393 |
| i | K | A | E | A | K | K | 101.107 | 44.049 | 102.054 | 44.049 | 101.107 | 101.107 |
| | 6 | 5 | 4 | 3 | 2 | 1 | Lys | Lys | Ala | Glu | Ala | Lys |

| | K | A | E | A | K | K | Ion | Lys | Ala | Glu | Ala | Lys | Lys |
|---|---|---|---|---|---|---|---|---|---|---|---|---|---|
| | 1 | 2 | 3 | 4 | 5 | 6 | | 1 | 2 | 3 | 4 | 5 | 6 |
| a | K | A | E | A | K | K | a | 101.107 | 172.144 | 301.187 | 372.224 | 500.319 | 628.414 |
| a-17 | K | A | E | A | K | K | a-17 | 84.081 | 155.118 | 284.160 | 355.198 | 483.293 | 611.388 |
| a-18 | K | A | E | A | K | K | a-18 | 83.097 | 154.134 | 283.176 | 354.214 | 482.309 | 610.404 |
| b | K | A | E | A | K | K | b | 129.102 | 200.139 | 329.182 | 400.219 | 528.314 | 656.409 |
| b-17 | K | A | E | A | K | K | b-17 | 112.076 | 183.113 | 312.155 | 383.193 | 511.287 | 639.382 |
| b-18 | K | A | E | A | K | K | b-18 | 111.092 | 182.129 | 311.171 | 382.208 | 510.303 | 638.398 |
| b+18 | K | A | E | A | K | K | b+18 | 147.113 | 218.150 | 347.193 | 418.230 | 546.325 | 674.420 |
| c | K | A | E | A | K | K | c | 146.129 | 217.166 | 346.208 | 417.246 | 545.341 | 673.436 |
| x | K | A | E | A | K | K | x | 173.092 | 301.187 | 372.224 | 501.267 | 572.304 | 700.399 |
| y | K | A | E | A | K | K | y | 147.113 | 275.208 | 346.245 | 475.287 | 546.325 | 674.420 |
| z | K | A | E | A | K | K | z | 130.086 | 258.181 | 329.218 | 458.261 | 529.298 | 657.393 |
| i | K | A | E | A | K | K | i | 101.107 | 44.049 | 102.054 | 44.049 | 101.107 | 101.107 |
| | 6 | 5 | 4 | 3 | 2 | 1 | | Lys | Lys | Ala | Glu | Ala | Lys |

FIG.6b-2B

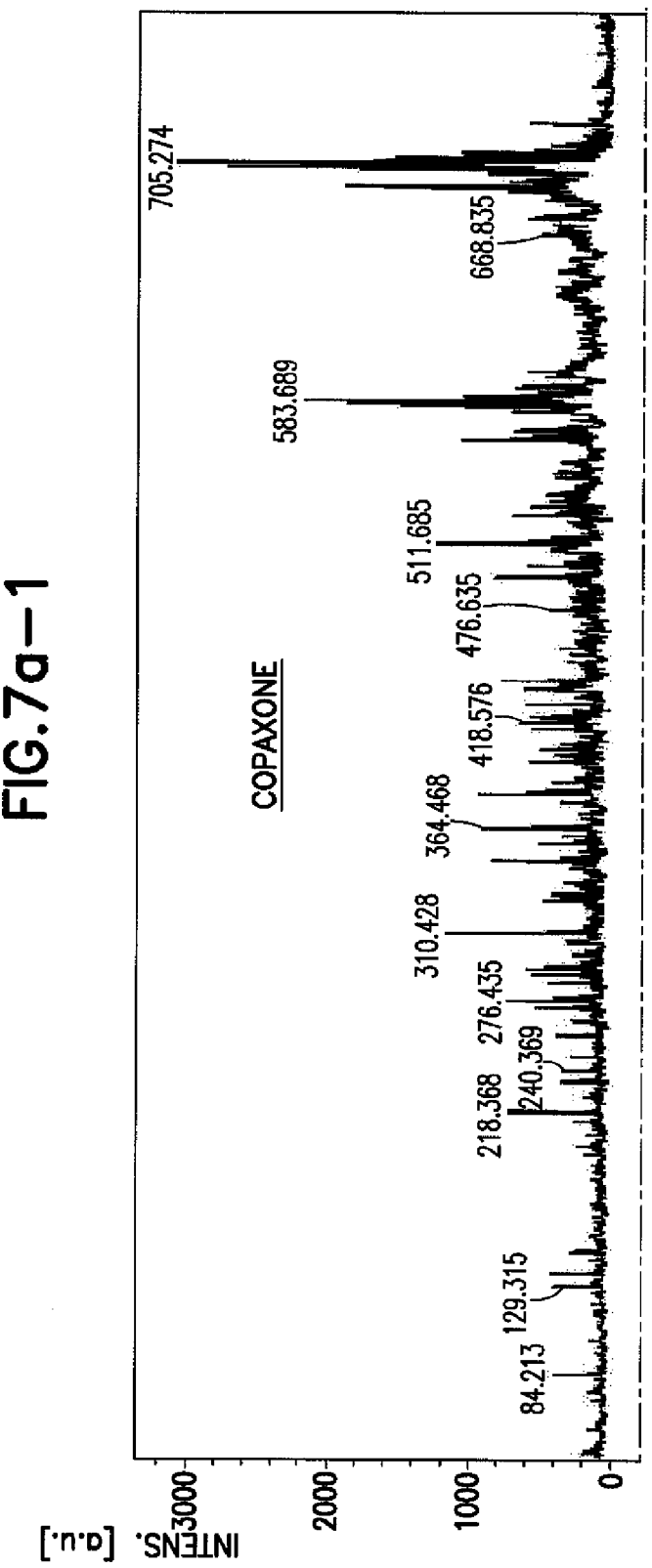

| Ion | E | E | A | A | Y | K | Glu | Glu | Ala | Ala | Tyr | Lys |
|-----|---|---|---|---|---|---|-----|-----|-----|-----|-----|-----|
|     | 1 | 2 | 3 | 4 | 5 | 6 | 1   | 2   | 3   | 4   | 5   | 6   |
| a   | E | E | A | A | Y | K | 102.055 | 231.098 | 302.135 | 373.172 | 536.235 | 664.330 |
| a-17 | E | E | A | A | Y | K | 85.028 | 214.071 | 285.108 | 356.145 | 519.209 | 647.304 |
| a-18 | E | E | A | A | Y | K | 84.044 | 213.087 | 284.124 | 355.161 | 518.225 | 646.320 |
| b   | E | E | A | A | Y | K | 130.050 | 259.092 | 330.130 | 401.167 | 564.230 | 692.325 |
| b-17 | E | E | A | A | Y | K | 113.023 | 242.066 | 313.103 | 384.140 | 547.203 | 675.298 |
| b-18 | E | E | A | A | Y | K | 112.039 | 241.082 | 312.119 | 383.156 | 546.219 | 674.314 |
| b+18 | E | E | A | A | Y | K | 148.060 | 277.103 | 348.140 | 419.177 | 582.241 | 710.336 |
| c   | E | E | A | A | Y | K | 147.076 | 276.119 | 347.156 | 418.193 | 581.257 | 709.352 |
| x   | E | E | A | A | Y | K | 173.092 | 336.155 | 407.193 | 478.230 | 607.272 | 736.315 |
| y   | E | E | A | A | Y | K | 147.113 | 310.176 | 381.213 | 452.250 | 581.293 | 710.336 |
| z   | E | E | A | A | Y | K | 130.086 | 293.150 | 364.187 | 435.224 | 564.266 | 693.309 |
| i   | E | E | A | A | Y | K | 148.060 | 102.054 | 44.049 | 44.049 | 136.075 | 101.107 |
|     | 6 | 5 | 4 | 3 | 2 | 1 | Lys | Tyr | Ala | Ala | Glu | Glu |

| Ion | E 1 | E 2 | A 3 | A 4 | Y 5 | K 6 | Glu 1 | Glu 2 | Ala 3 | Ala 4 | Tyr 5 | Lys 6 |
|---|---|---|---|---|---|---|---|---|---|---|---|---|
| a | E | E | A | A | Y | K | 102.055 | 231.098 | 302.135 | 373.172 | 536.235 | 664.330 |
| a-17 | E | E | A | A | Y | K | 85.028 | 214.071 | 285.108 | 356.145 | 519.209 | 647.304 |
| a-18 | E | E | A | A | Y | K | 84.044 | 213.087 | 284.124 | 355.161 | 518.225 | 646.320 |
| b | E | E | A | A | Y | K | 130.050 | 259.092 | 330.130 | 401.167 | 564.230 | 692.325 |
| b-17 | E | E | A | A | Y | K | 113.023 | 242.066 | 313.103 | 384.140 | 547.203 | 675.298 |
| b-18 | E | E | A | A | Y | K | 112.039 | 241.082 | 312.119 | 383.156 | 546.219 | 674.314 |
| b+18 | E | E | A | A | Y | K | 148.060 | 277.103 | 348.140 | 419.177 | 582.241 | 710.336 |
| c | E | E | A | A | Y | K | 147.076 | 276.119 | 347.156 | 418.193 | 581.257 | 709.352 |
| x | E | E | A | A | Y | K | 173.092 | 336.155 | 407.193 | 478.230 | 607.272 | 736.315 |
| y | E | E | A | A | Y | K | 147.113 | 310.176 | 381.213 | 452.250 | 581.293 | 710.336 |
| z | E | E | A | A | Y | K | 130.086 | 293.150 | 364.187 | 435.224 | 564.266 | 693.309 |
| i | E | E | A | A | Y | K | 102.055 | 102.054 | 44.049 | 44.049 | 136.075 | 101.107 |
|  | 6 | 5 | 4 | 3 | 2 | 1 | Lys | Tyr | Ala | Ala | Glu | Glu |

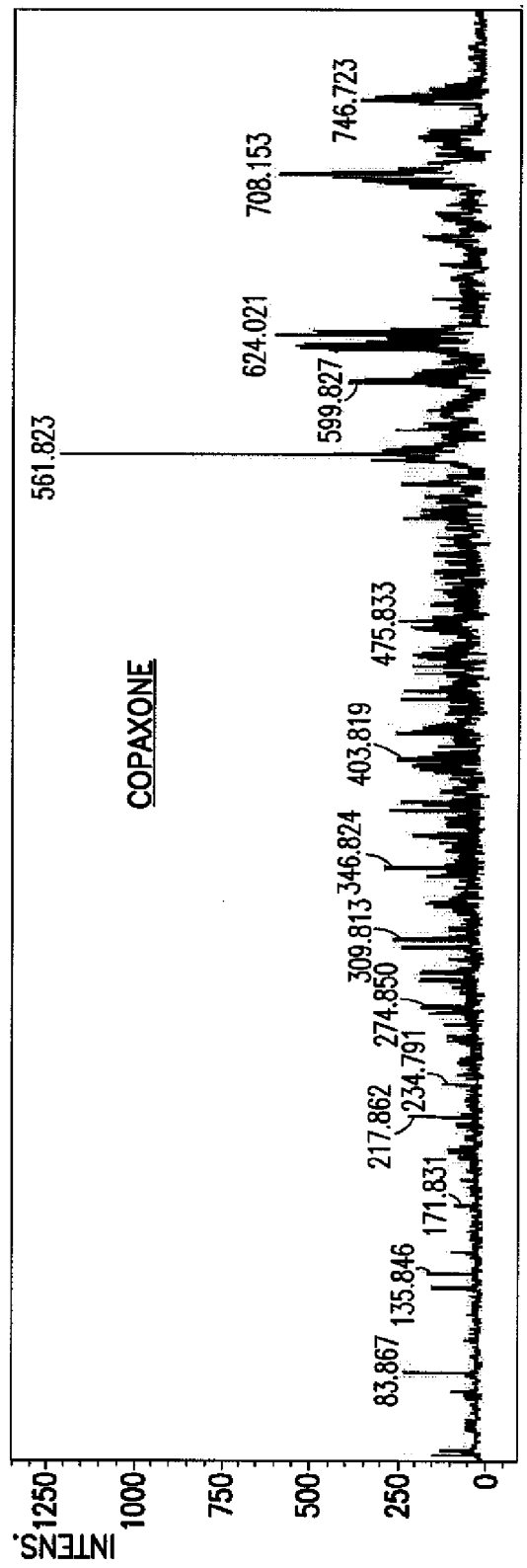

| Ion | K | A | E | A | K | A | K |   | Lys | Ala | Glu | Ala | Lys | Ala | Lys |
|---|---|---|---|---|---|---|---|---|---|---|---|---|---|---|---|
|   | 1 | 2 | 3 | 4 | 5 | 6 | 7 |   | 1 | 2 | 3 | 4 | 5 | 6 | 7 |
| a | K | A | E | A | K | A | K |   | 101.107 | 172.144 | 301.187 | 372.224 | 500.319 | 571.356 | 699.451 |
| a-17 | K | A | E | A | K | A | K |   | 84.081 | 155.118 | 284.160 | 355.198 | 483.293 | 554.330 | 682.425 |
| a-18 | K | A | E | A | K | A | K |   | 83.097 | 154.134 | 283.176 | 354.214 | 482.309 | 553.346 | 681.441 |
| b | K | A | E | A | K | A | K |   | 129.102 | 200.139 | 329.182 | 400.219 | 528.314 | 599.351 | 727.446 |
| b-17 | K | A | E | A | K | A | K |   | 112.076 | 183.113 | 312.155 | 383.193 | 511.287 | 582.325 | 710.420 |
| b-18 | K | A | E | A | K | A | K |   | 111.092 | 182.129 | 311.171 | 382.208 | 510.303 | 581.341 | 709.436 |
| b+18 | K | A | E | A | K | A | K |   | 147.113 | 218.150 | 347.193 | 418.230 | 546.325 | 617.362 | 745.457 |
| c | K | A | E | A | K | A | K |   | 146.129 | 217.166 | 346.208 | 417.246 | 545.341 | 616.378 | 744.473 |
| x | K | A | E | A | K | A | K |   | 173.092 | 244.129 | 372.224 | 443.261 | 572.304 | 643.341 | 771.436 |
| y | K | A | E | A | K | A | K |   | 147.113 | 218.150 | 346.245 | 417.282 | 546.325 | 617.362 | 745.457 |
| z | K | A | E | A | K | A | K |   | 130.086 | 201.123 | 329.218 | 400.255 | 529.298 | 600.335 | 728.430 |
| i | K | A | E | A | K | A | K |   | 101.107 | 44.049 | 102.054 | 44.049 | 101.107 | 44.049 | 101.107 |
|   | 7 | 6 | 5 | 4 | 3 | 2 | 1 |   | Lys | Ala | Lys | Ala | Glu | Ala | Lys |

| Ion | | | | | | | | Lys 1 | Ala 2 | Glu 3 | Ala 4 | Lys 5 | Ala 6 | Lys 7 |
|---|---|---|---|---|---|---|---|---|---|---|---|---|---|---|
| | K 1 | A 2 | E 3 | A 4 | K 5 | A 6 | K 7 | | | | | | | |
| a | K | A | E | A | K | A | K | 101.107 | 172.144 | 301.187 | 372.224 | 500.319 | 571.356 | 699.451 |
| a-17 | K | A | E | A | K | A | K | 84.081 | 155.118 | 284.160 | 355.198 | 483.293 | 554.330 | 682.425 |
| a-18 | K | A | E | A | K | A | K | 83.097 | 154.134 | 283.176 | 354.214 | 482.309 | 553.346 | 681.441 |
| b | K | A | E | A | K | A | K | 129.102 | 200.139 | 329.182 | 400.219 | 528.314 | 599.351 | 727.446 |
| b-17 | K | A | E | A | K | A | K | 112.076 | 183.113 | 312.155 | 383.193 | 511.287 | 582.325 | 710.420 |
| b-18 | K | A | E | A | K | A | K | 111.092 | 182.129 | 311.171 | 382.208 | 510.303 | 581.341 | 709.436 |
| b+18 | K | A | E | A | K | A | K | 147.113 | 218.150 | 347.193 | 418.230 | 546.325 | 617.362 | 745.457 |
| c | K | A | E | A | K | A | K | 146.129 | 217.166 | 346.208 | 417.246 | 545.341 | 616.378 | 744.473 |
| x | K | A | E | A | K | A | K | 173.092 | 244.129 | 372.224 | 443.261 | 572.304 | 643.341 | 771.436 |
| y | K | A | E | A | K | A | K | 147.113 | 218.150 | 346.245 | 417.282 | 546.325 | 617.362 | 745.457 |
| z | K | A | E | A | K | A | K | 130.086 | 201.123 | 329.218 | 400.255 | 529.298 | 600.335 | 728.430 |
| i | K | A | E | A | K | A | K | 101.107 | 44.049 | 102.054 | 44.049 | 101.107 | 44.049 | 101.107 |
| | 7 | 6 | 5 | 4 | 3 | 2 | 1 | Lys | Ala | Lys | Ala | Glu | Ala | Lys |

FIG.8b-2B

| FIG.8b-2A |
|---|
| FIG.8b-2B |

FIG.8b-2

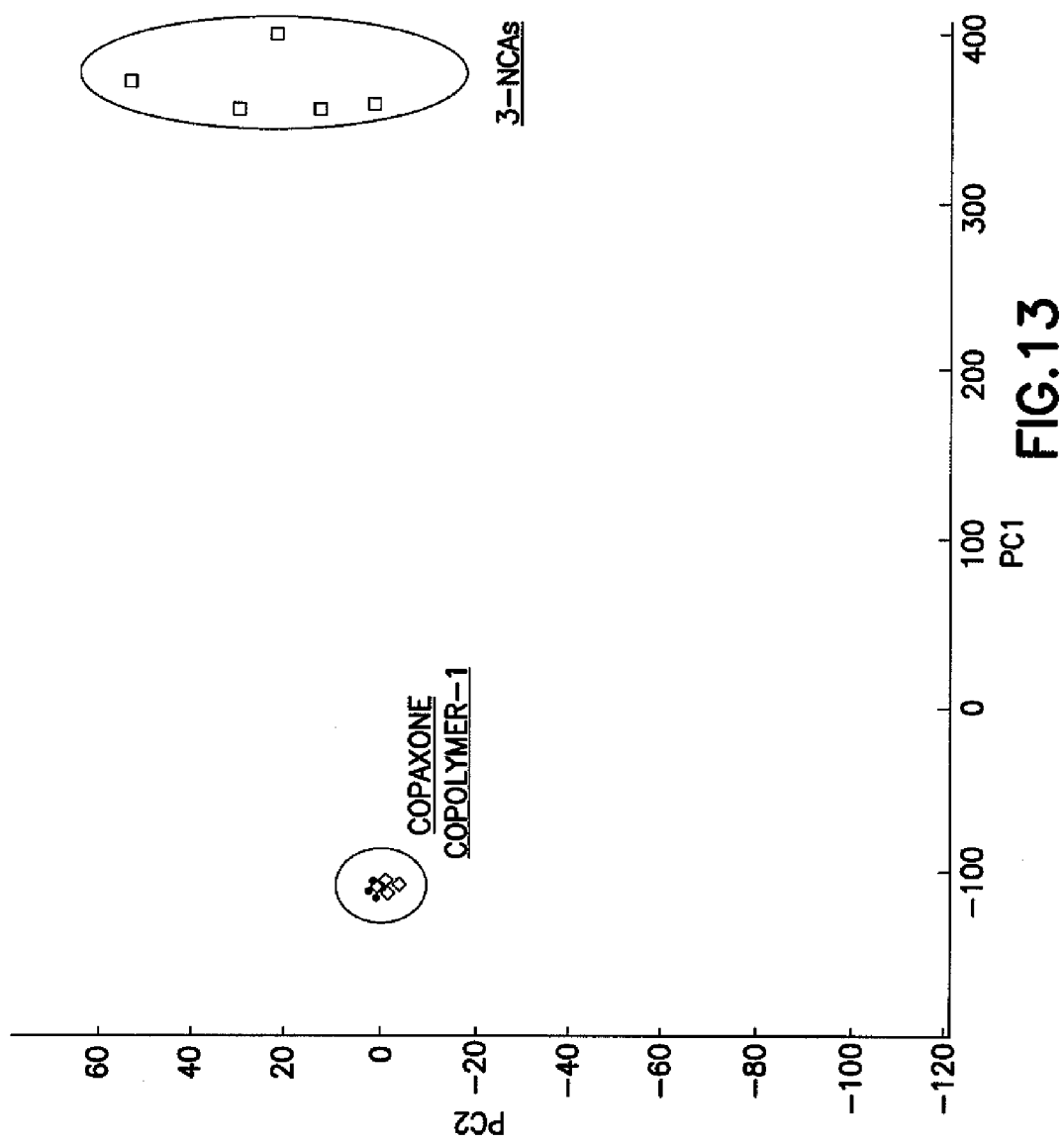

METHODS OF ANALYZING PEPTIDE MIXTURES

RELATED APPLICATIONS

This application claims priority from U.S. Provisional Patent Application Ser. No. 61/176,579 which was filed on May 8, 2009.

FIELD OF INVENTION

The present invention relates to the analytic method for characterizing, comparing and classifying peptides, peptide mixtures, polypeptide mixtures and biomolecules that comprise a polypeptide component by mass spectrometry. More particularly, the present invention provides an analytical/statistical method for characterizing and classifying complex peptides mixtures, polypeptide mixtures comprising several different amino acids, or biomolecules that comprise a polypeptide component.

DESCRIPTION OF THE RELATED ARTS

Copolymer-1 is a complex mixture of polypeptides prepared from the polymerization of the amino acids glutamic acid, lysine, alanine and tyrosine. Copolymer-1 also is known as glatiramer acetate and has the following structural formula:

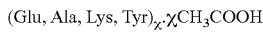

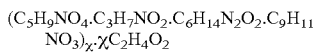

(Physician Desk reference, (2000))

Glatiramer acetate (GA) is the active ingredient of COPAXONE® (Teva Pharmaceutical Industries Ltd., Israel), which comprises the acetate salts of a synthetic polypeptide mixture containing four naturally occurring amino acids: L-glutamic acid, L-alanine, L-tyrosine, and L-lysine, with a reported average molar fraction of 0.141, 0.427, 0.095, and 0.338, respectively. The average molecular weight of COPAXONE® is between 4,700 and 11,000 daltons. Glatiramer acetate is an approved drug for the treatment of multiple sclerosis (MS). Processes for the preparation of glatiramer acetate are described in U.S. Pat. Nos. 3,849,550 and 5,800,808 and PCT International Publication No. WO 00/05250.

European Patent Application Publication No. 1 983 344 A1 discloses a method for digesting a single polypeptide standard by Trypsin and detecting its fragmentation by MADLDI-TOF. PCT International Publication No. WO 2008/135756 discloses digesting a single peptide standard by Trypsin, which provided the expected tryptic peptide fragments to be analyzed by tandem MS.

SUMMARY OF THE INVENTION

In contrast to prior art techniques, the present invention has shown that hydrolysis enzymes are used to digest a standard of a complex mixture of polypeptides, such as Glatiramer acetate, into several peptide fragments. The peptide fragments are analyzed by mass spectrometry (MS) and MS/MS. The mass spectrometric results of each sample are used as the fingerprint for comparison with other samples. The obtained mass spectra of the digests of the two samples are compared and served as the fingerprint of the respective sample.

Each peptide fragment detected by the first mass analyzer is selected and subjected to second mass spectrometric analysis (so called MS/MS analysis) to cleave the precursor peptide ions into even smaller fragments. The mass spectra obtained from MS/MS analysis are analyzed by the software such as Biotools to obtain the sequence of each peptide fragment. The results reveal the compositions and sequences of peptide ions detected in the first mass analyzer. Finally, the mass spectra of the digests of the samples are analyzed with statistic software (such as ClinProTool) for classification (such as 2D peaks distribution) through univariate peak rankings obtained from statistical tests (t-test, ANOVA . . . ). Grouping or distinction of different samples is also achieved by multivariate statistic (Principal Component Analysis, RCA). This strategic approach is to statistically compare the mass spectra of different products and differentiate the samples based on the resulting classification and locations of spots.

Figure 1B:
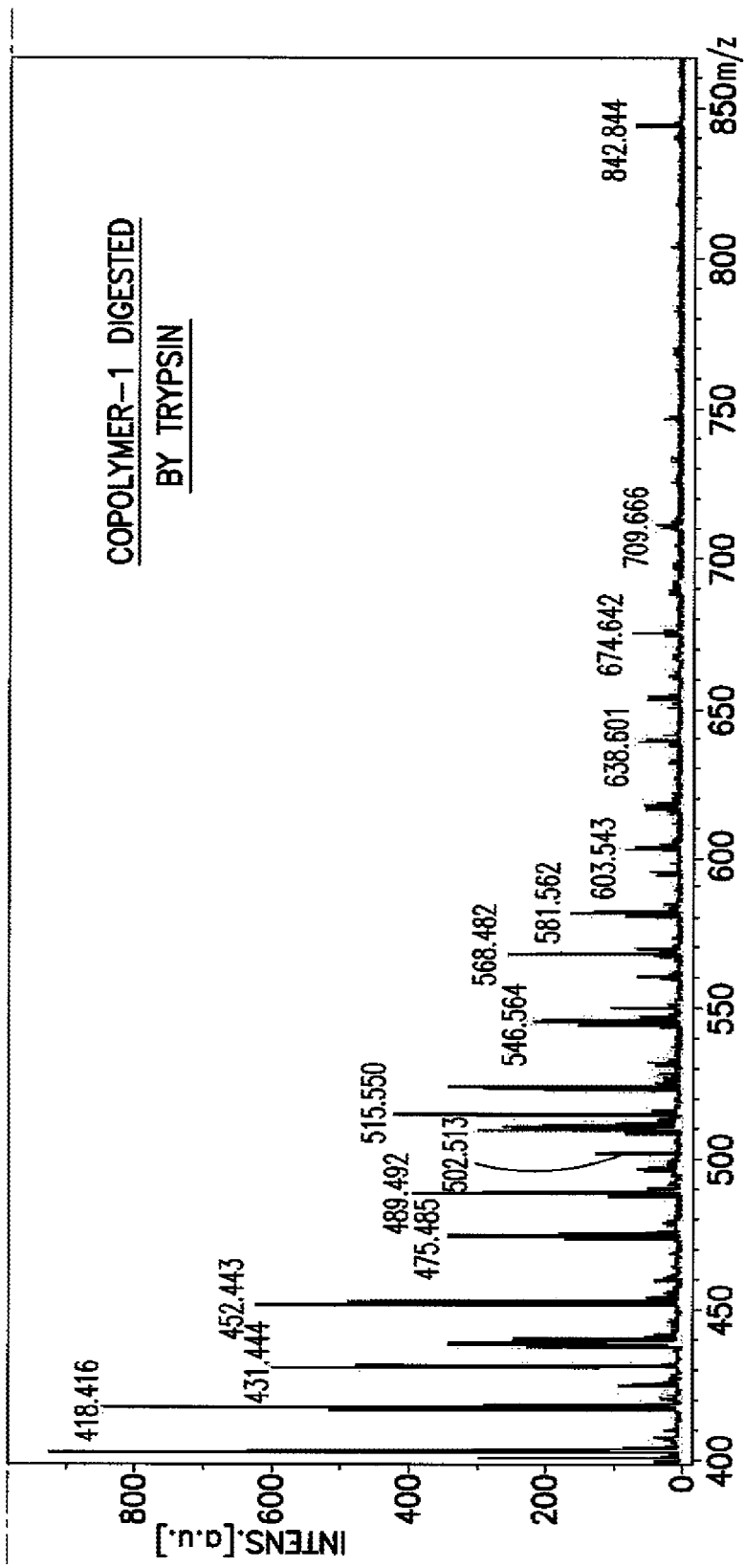
FIG. 1b show mass spectra of enzyme-digested Copolymer-1.
Figures 2, 2A:
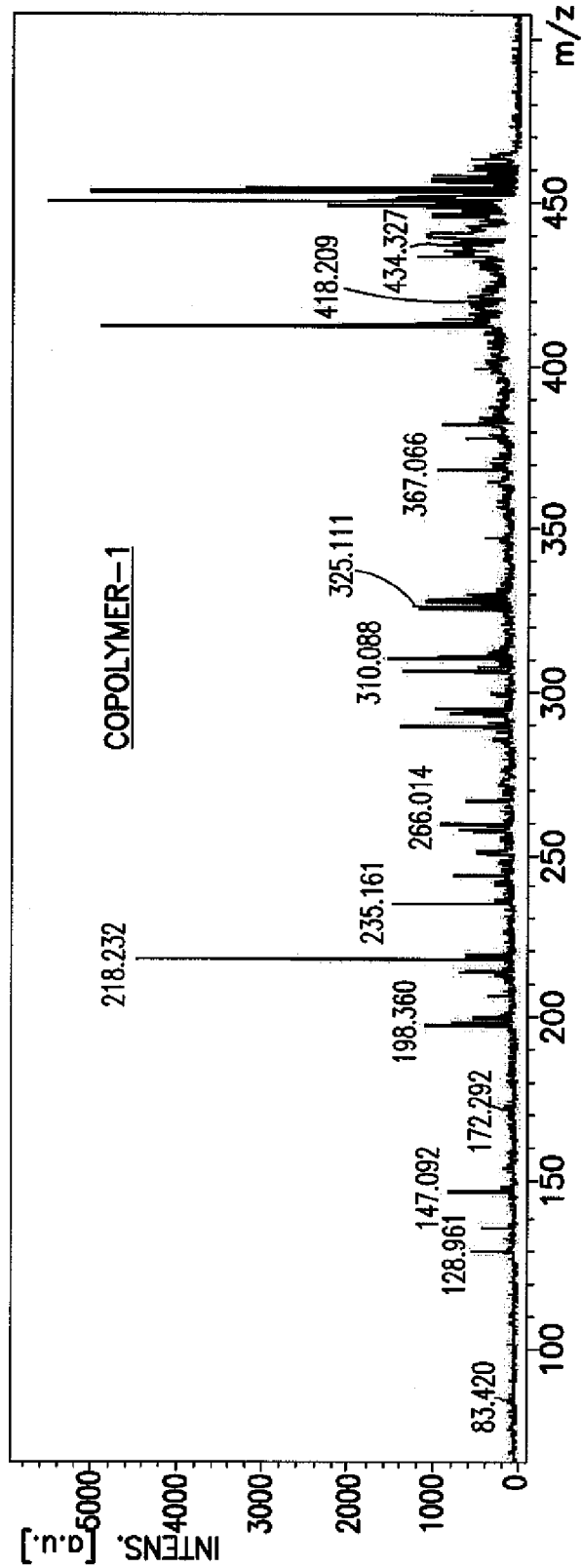
FIG. 2a-1 shows MS/MS spectra of the ion-m/z 452.44 recorded from enzyme-digested Copaxone.
Figures 1A, 2B:
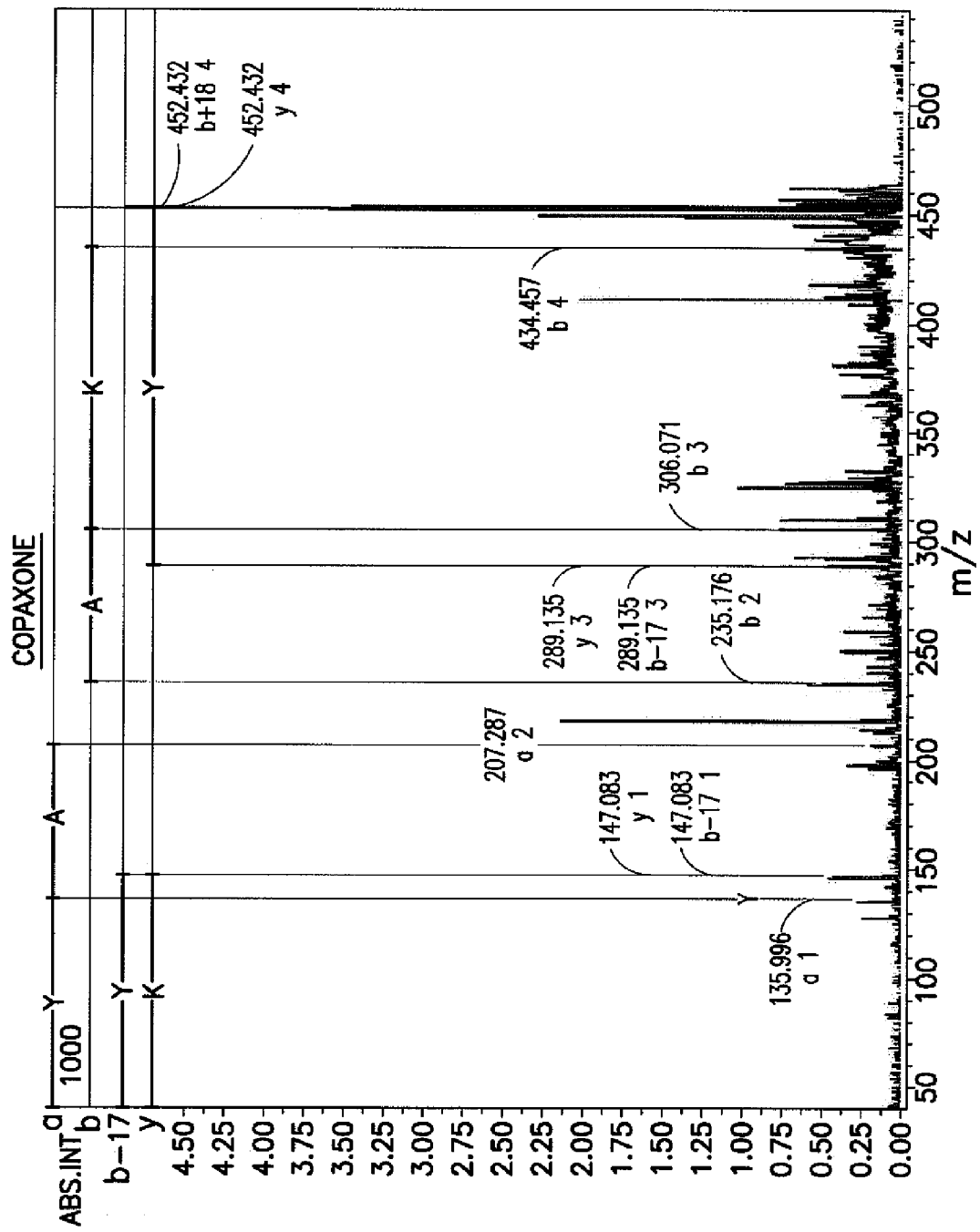
FIG. 1a shows mass spectra of enzyme-digested Copaxone.
Figures 2A, 2B:
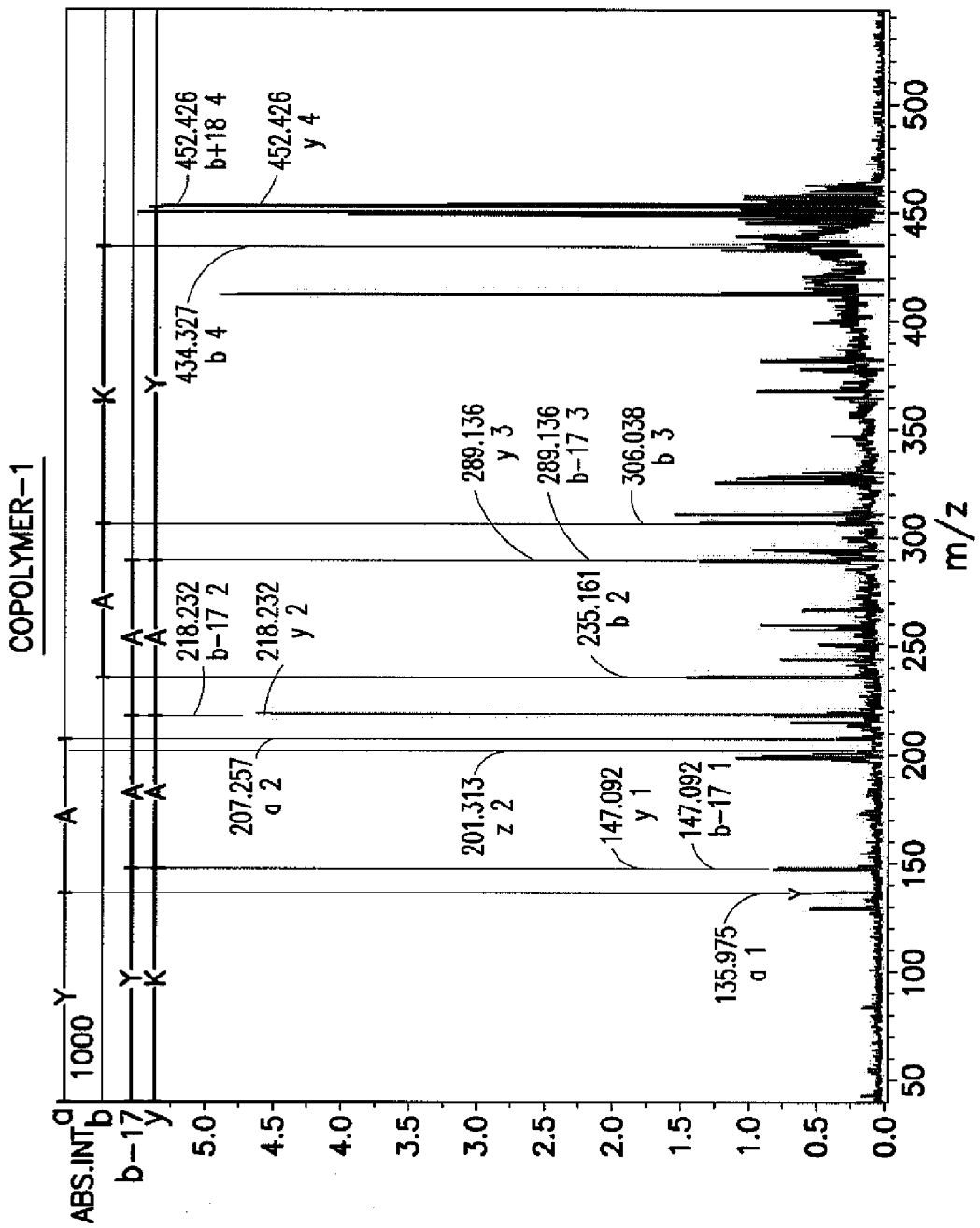
Figures 1, 3A:
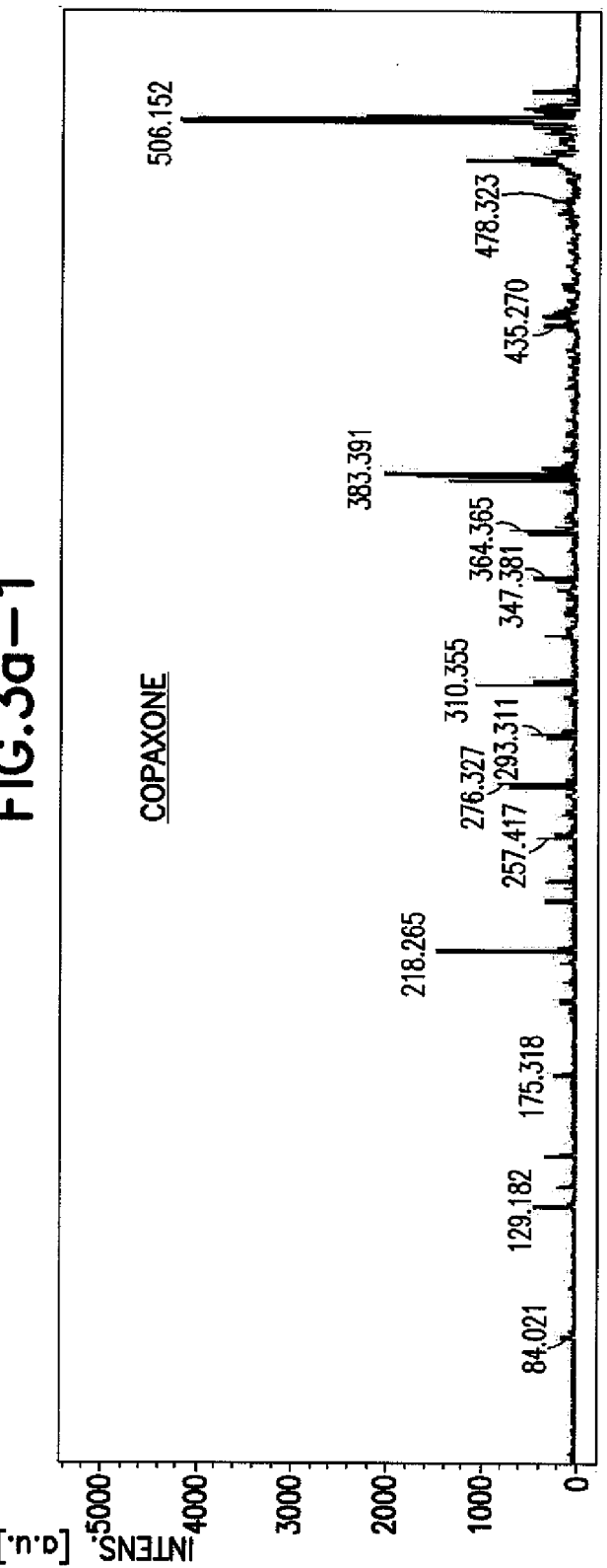
Figures 2, 3A:
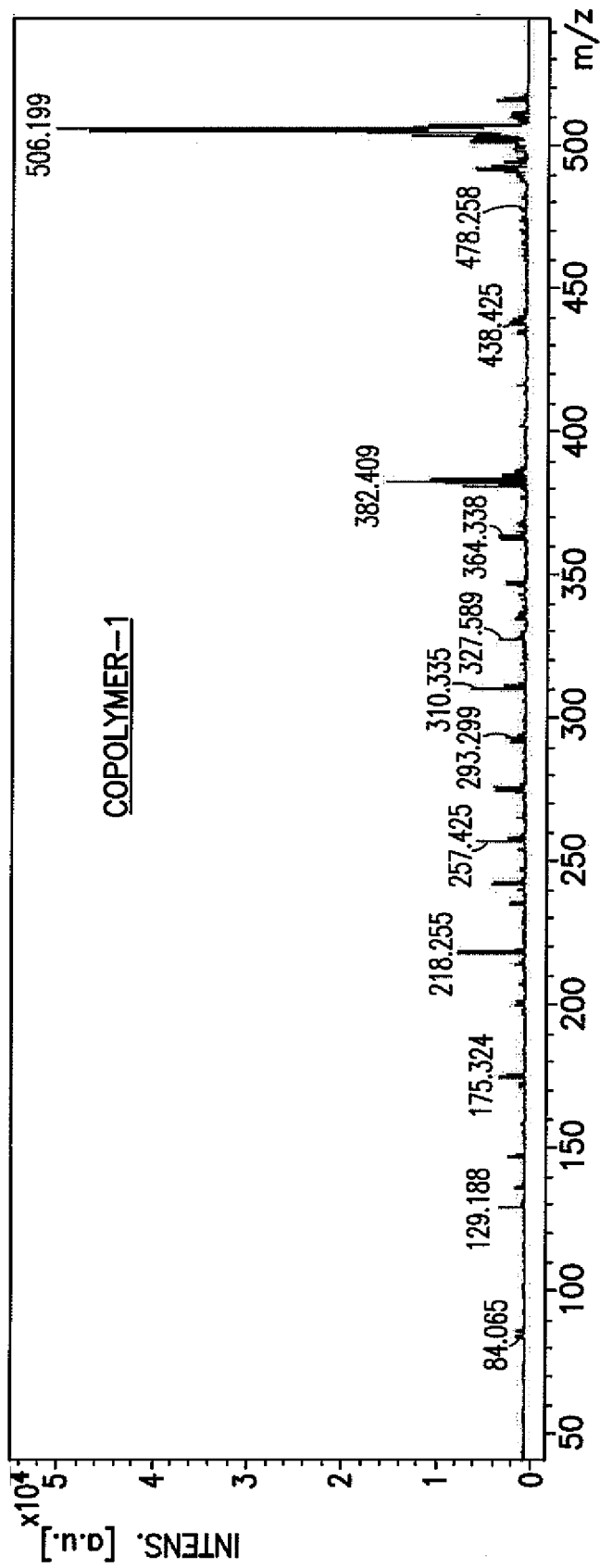
Figures 1A, 3B:
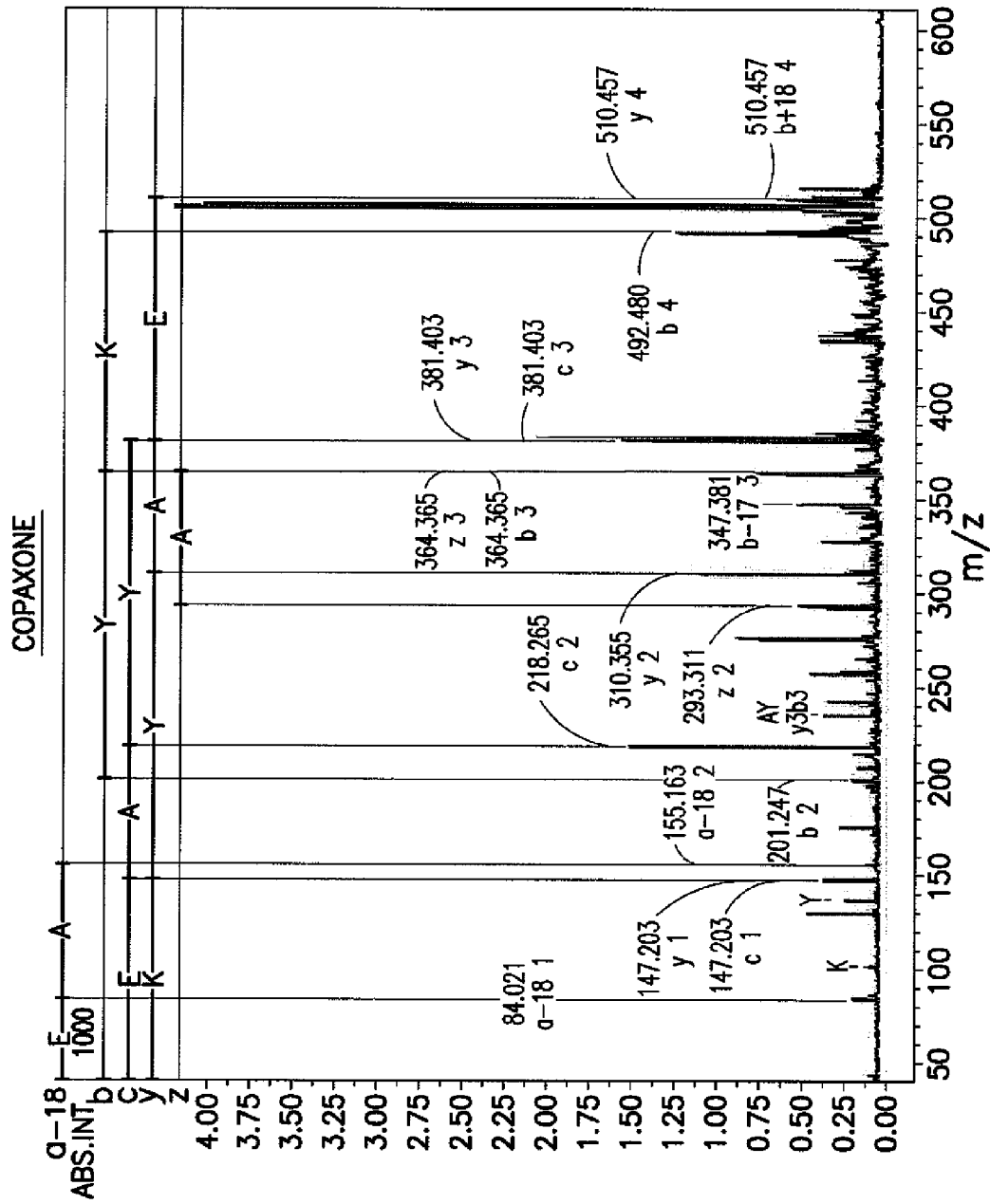
Figures 2A, 3B:
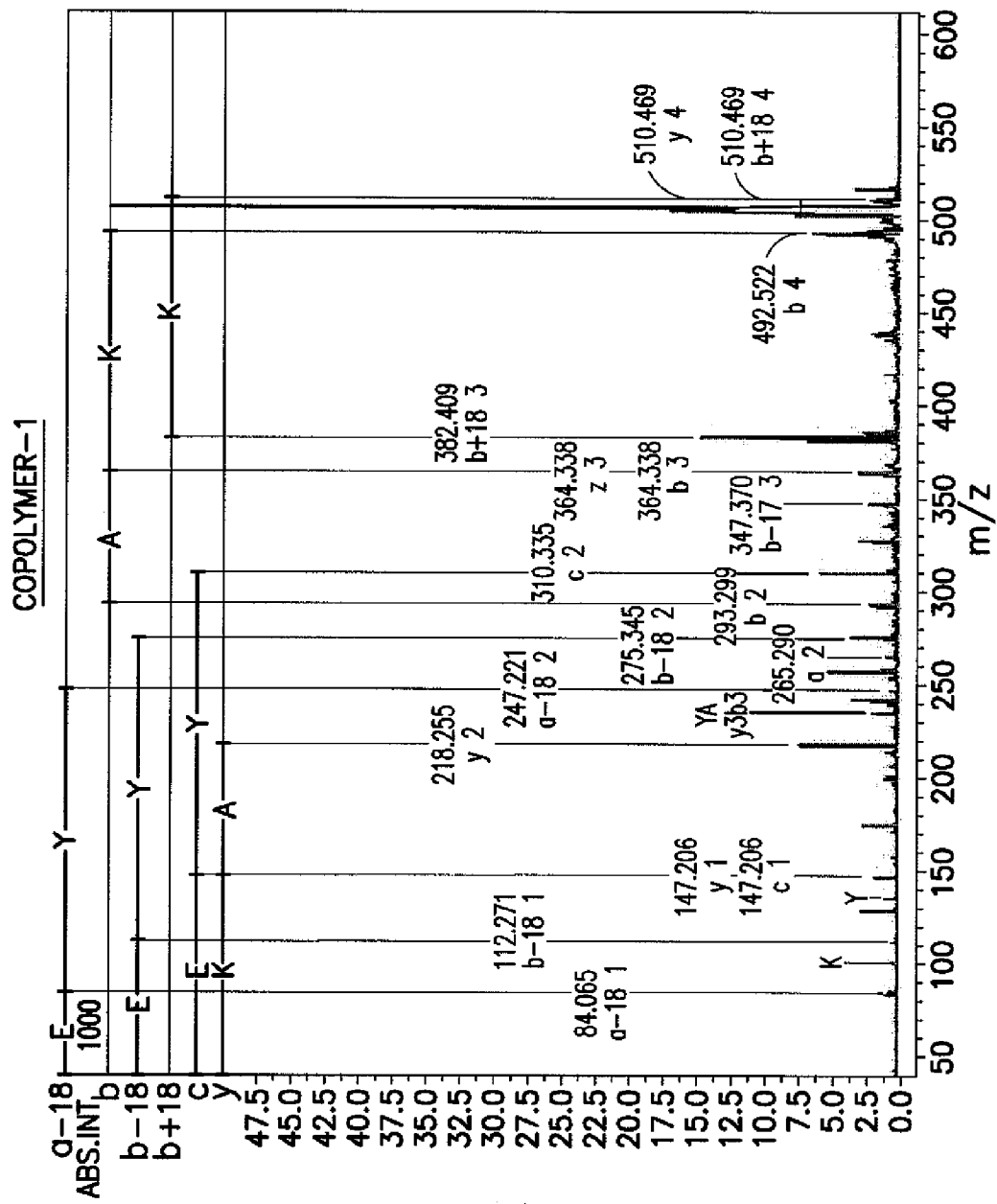
Figures 1A, 3C:
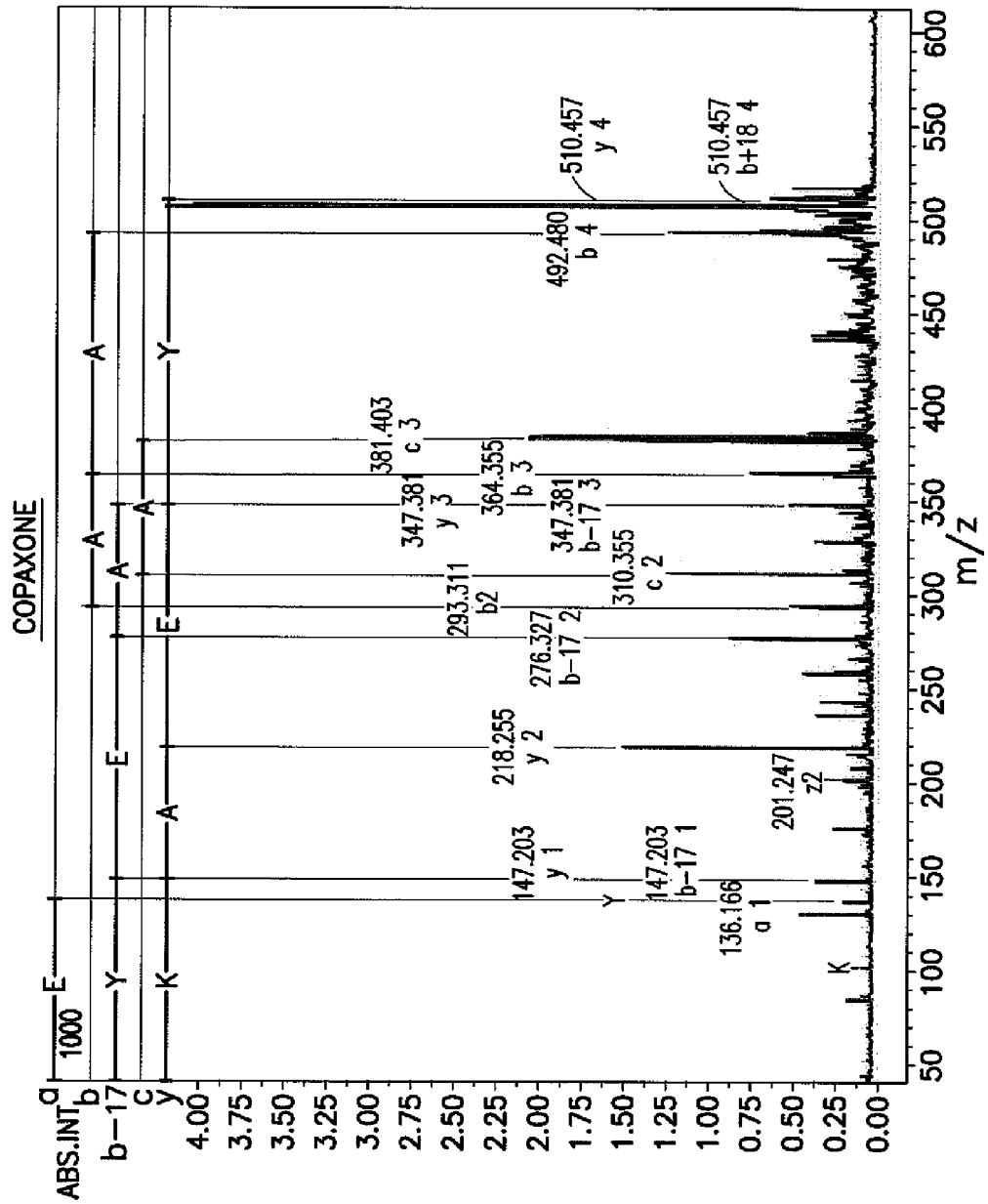
Figures 2A, 3C:
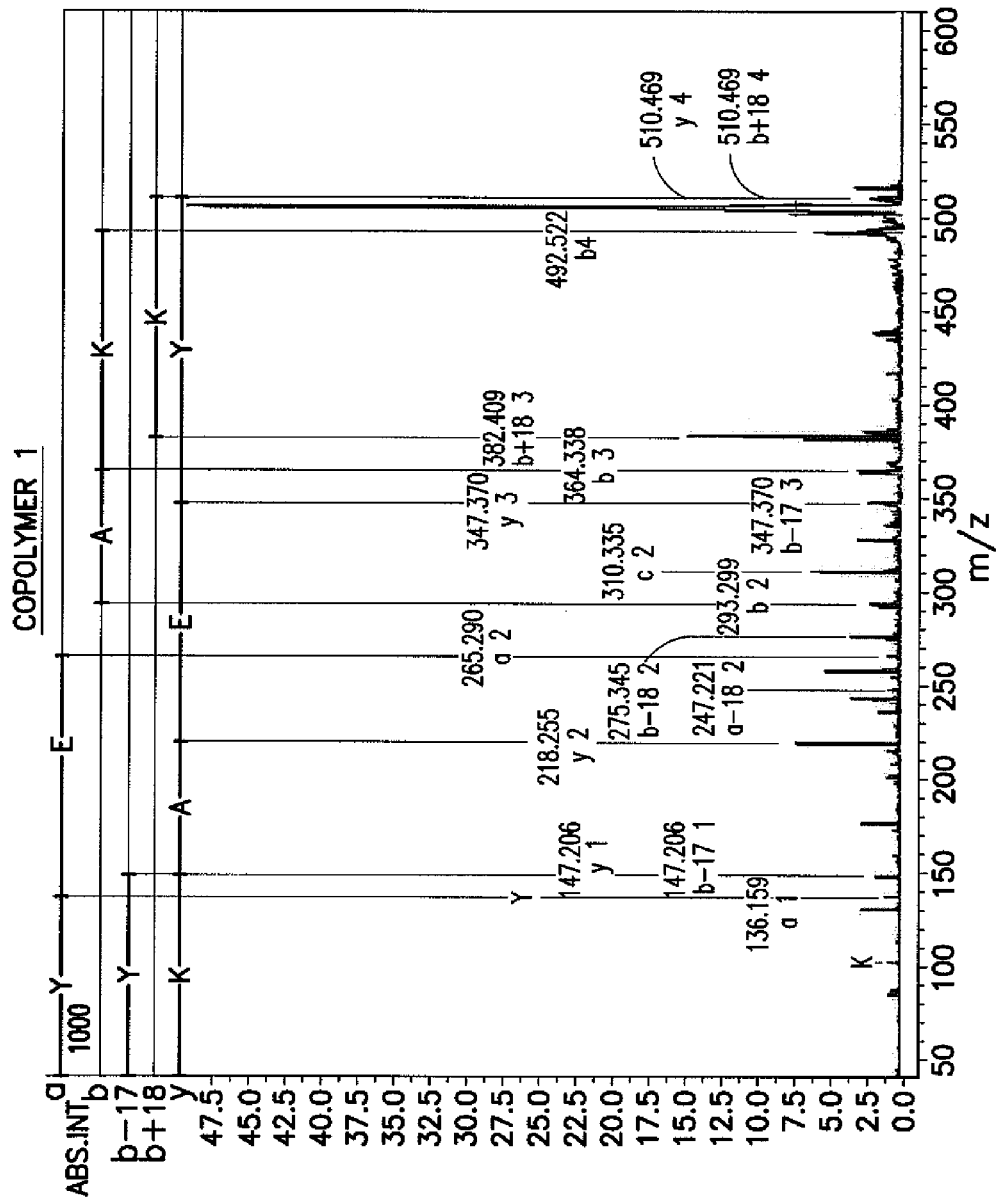
Figures 1, 4A:
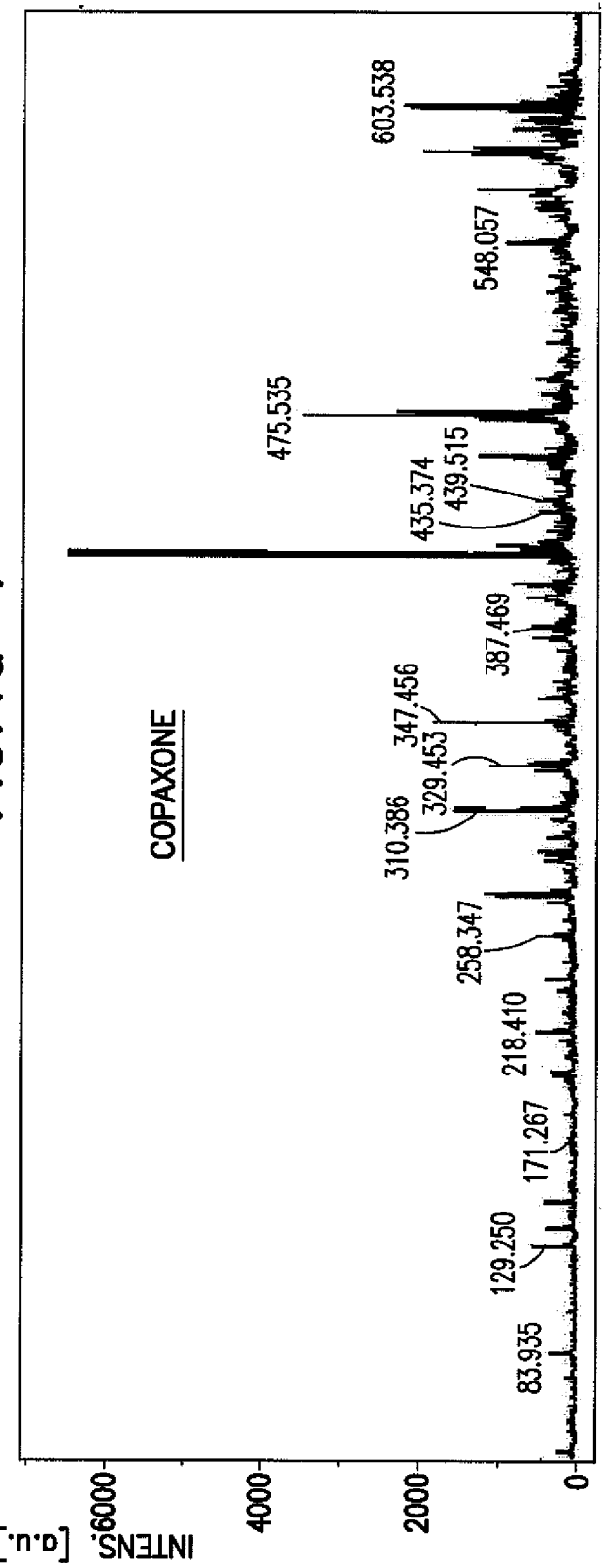
Figures 2, 4A:
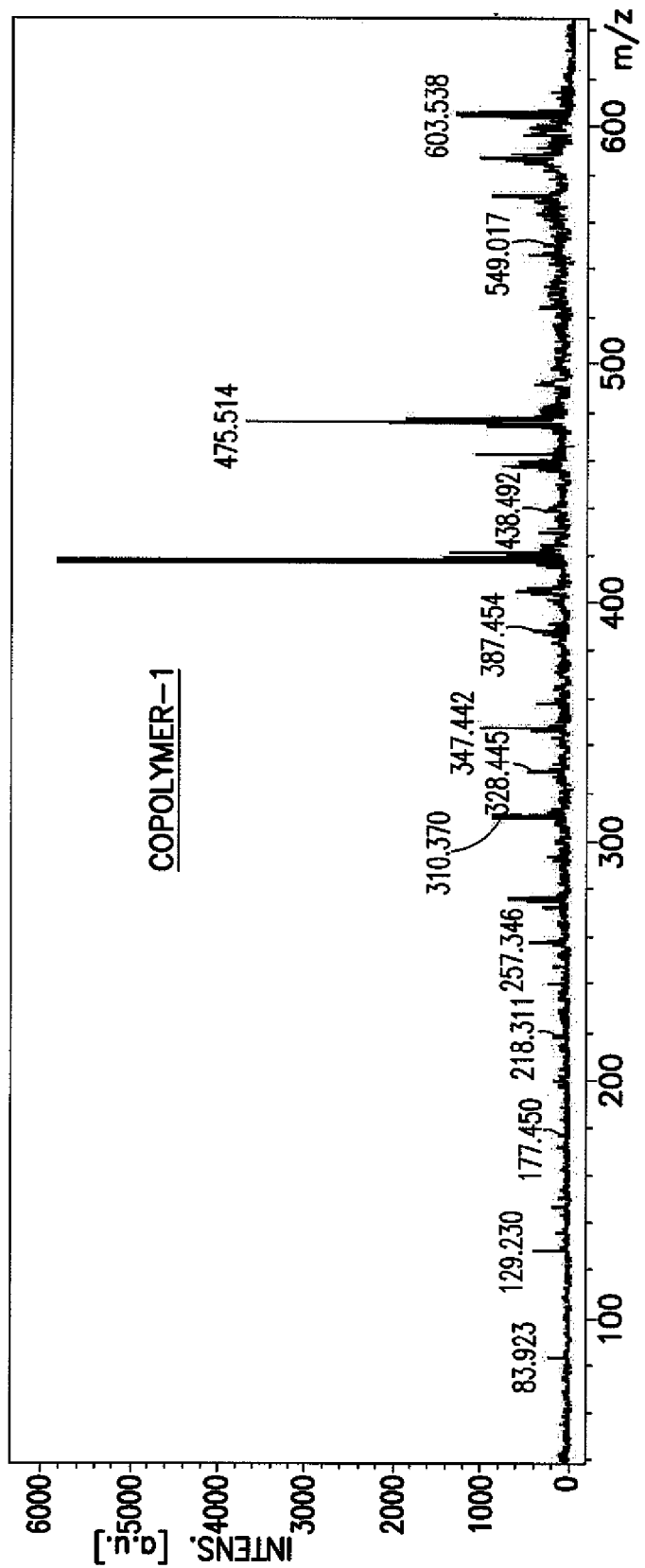
Figures 1A, 4B:
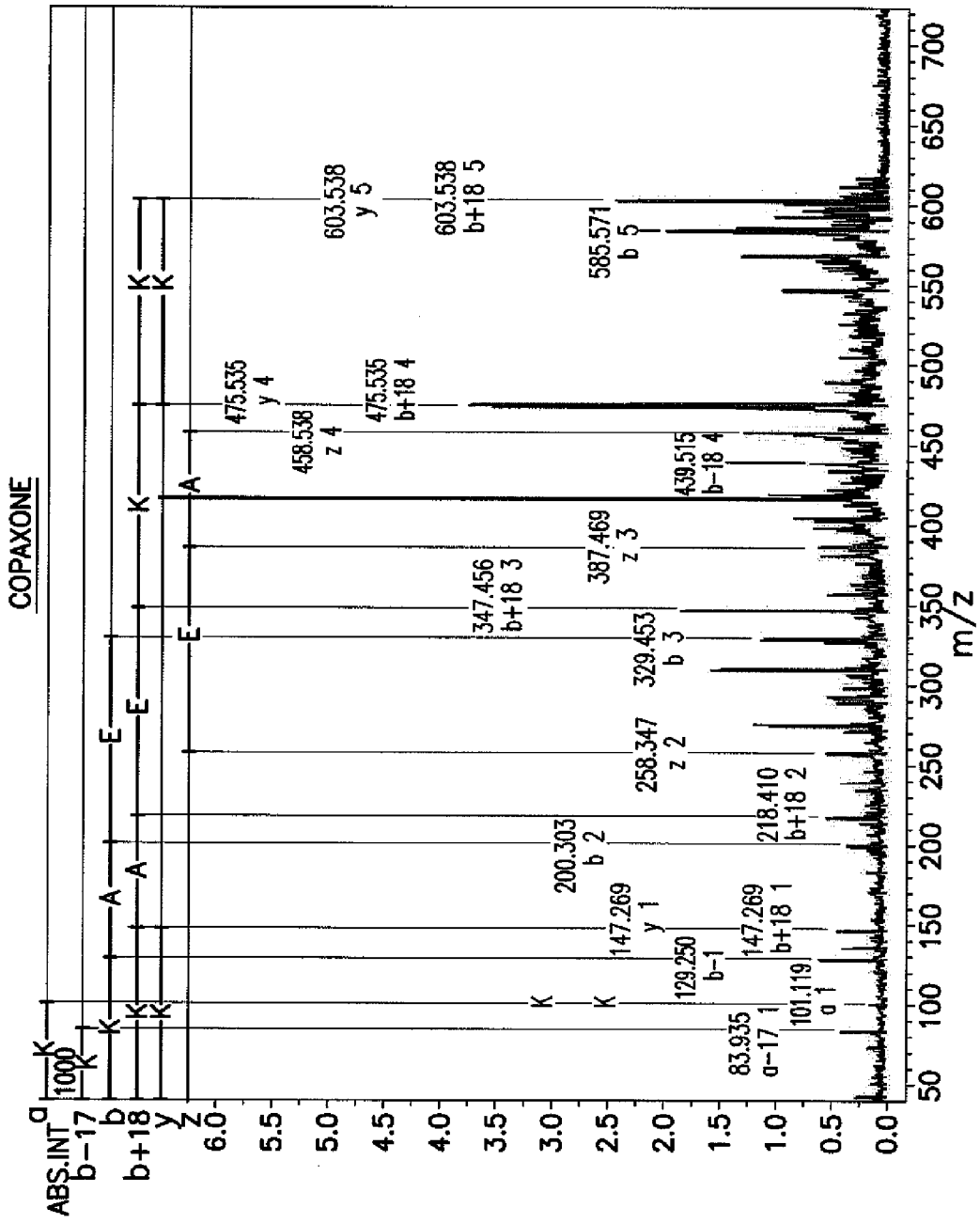
Figures 2A, 4B:
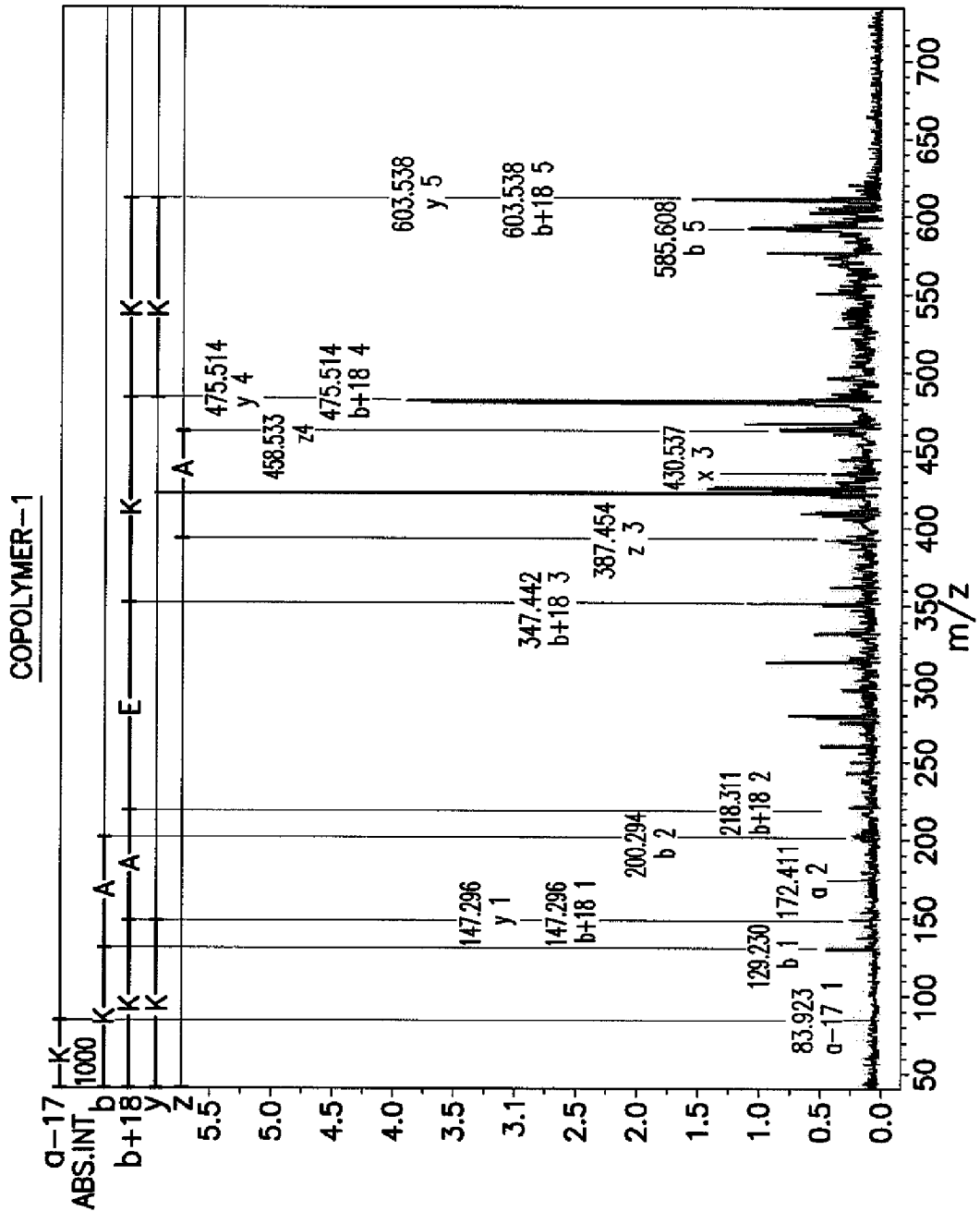
Figures 1, 5A:
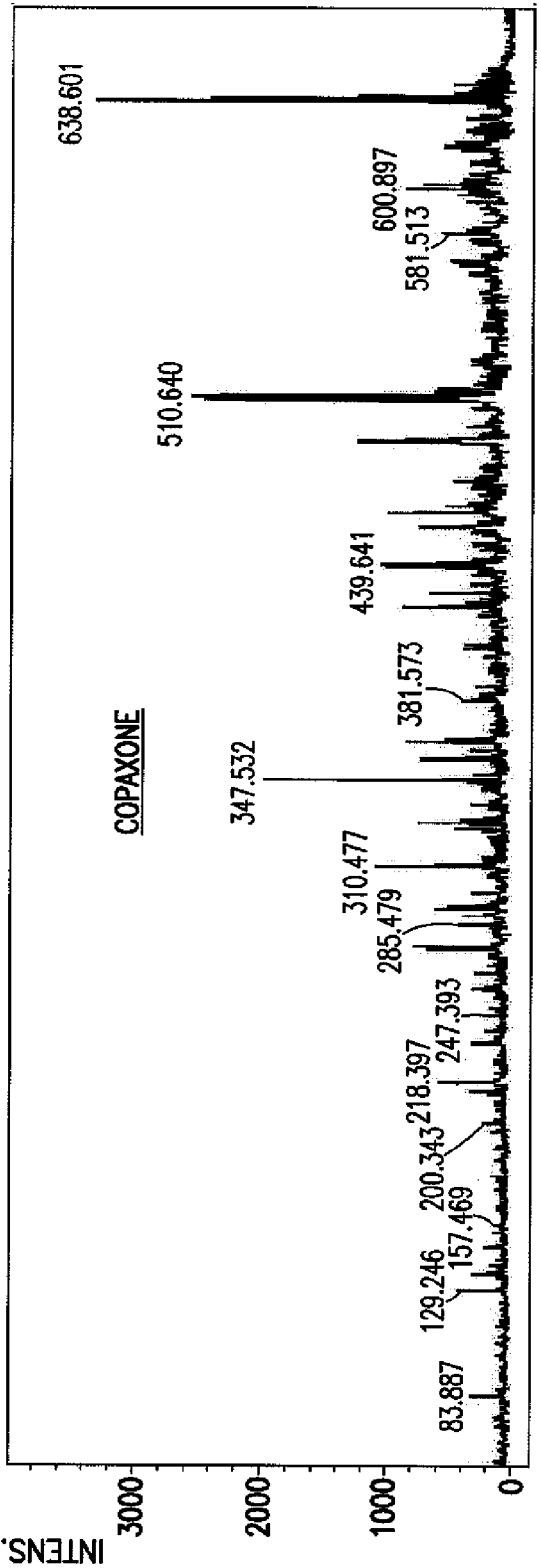
Figures 2, 5A:
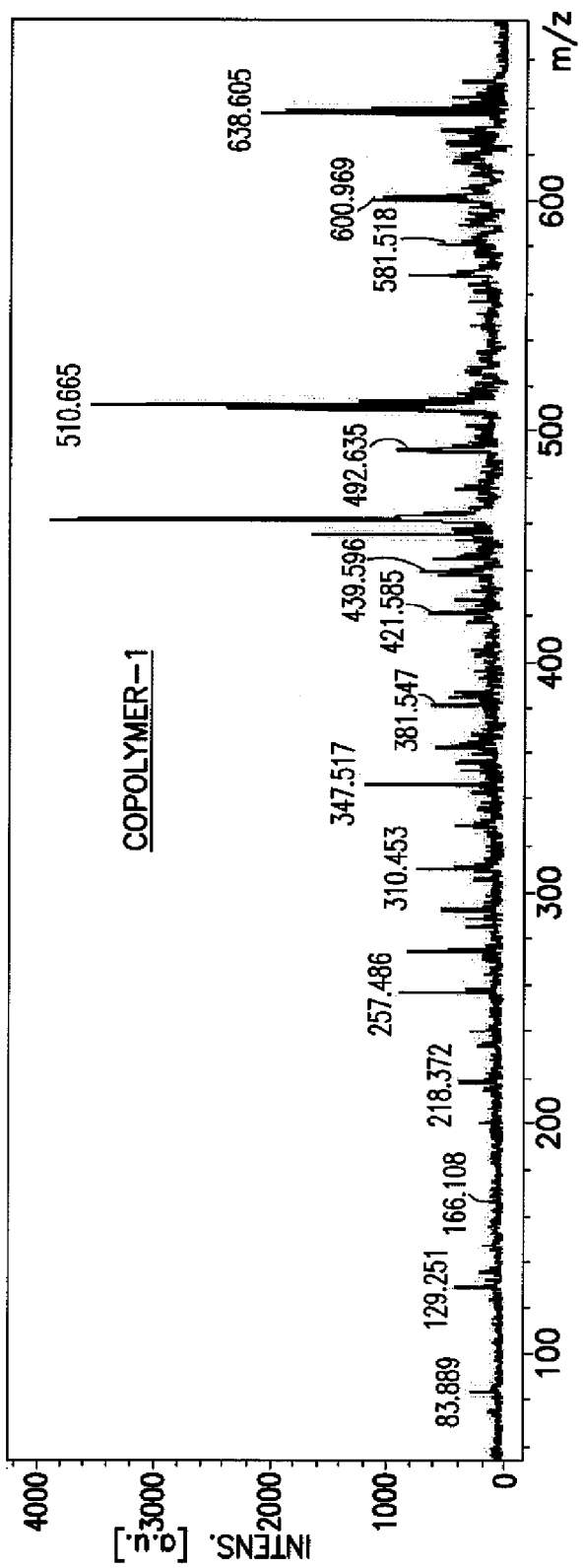
Figures 1A, 5B:
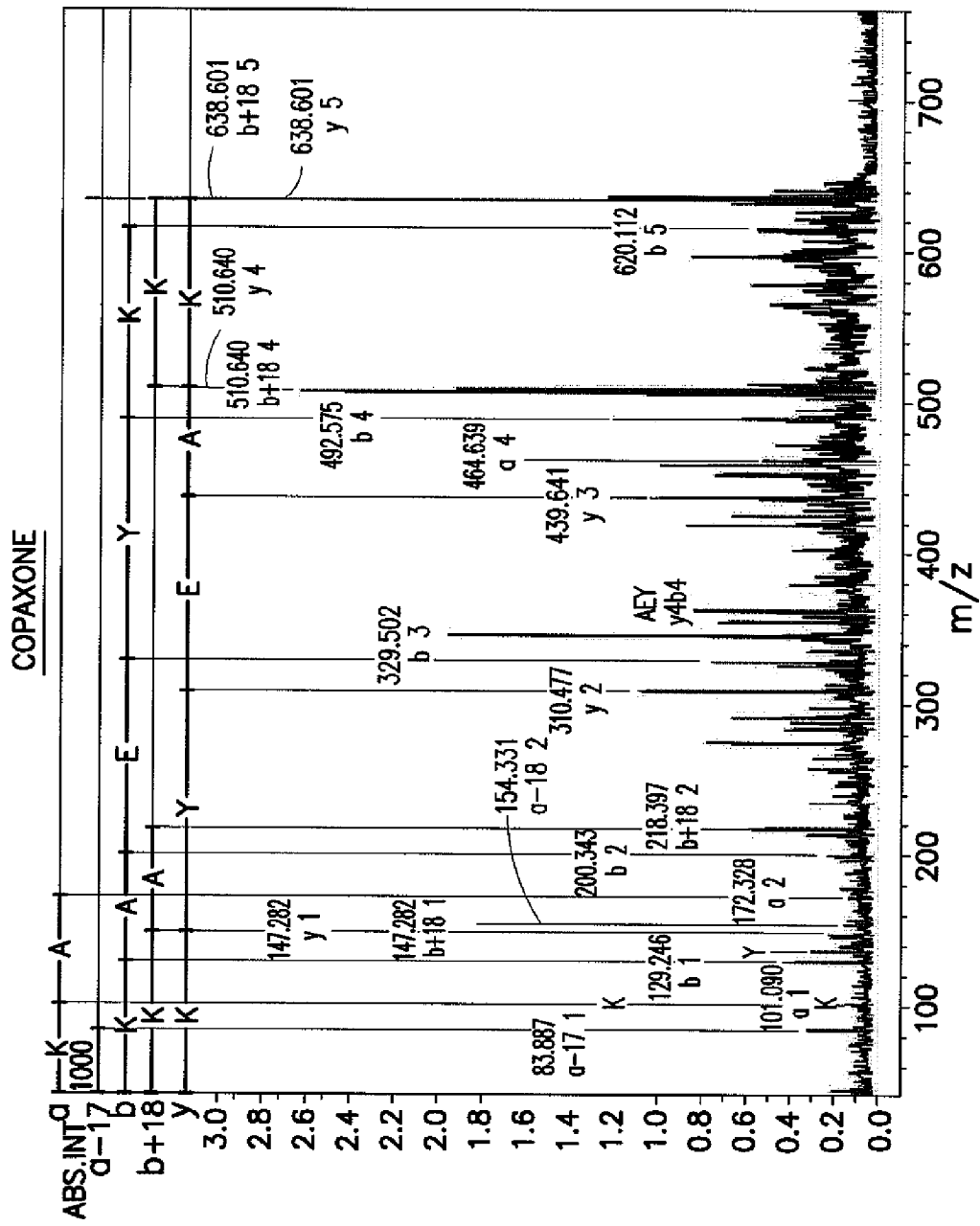
Figures 2A, 5B:
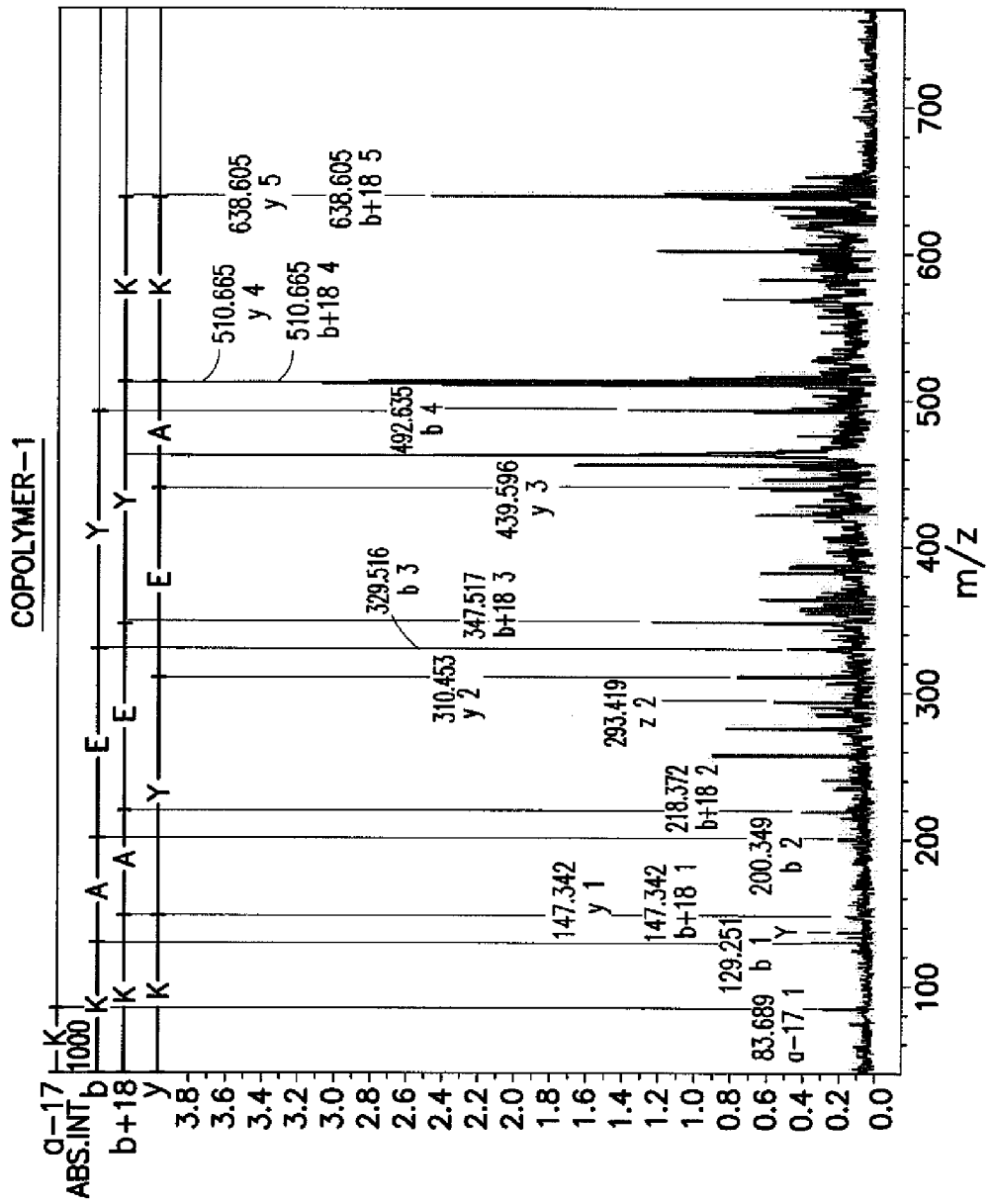
Figures 1, 6A:
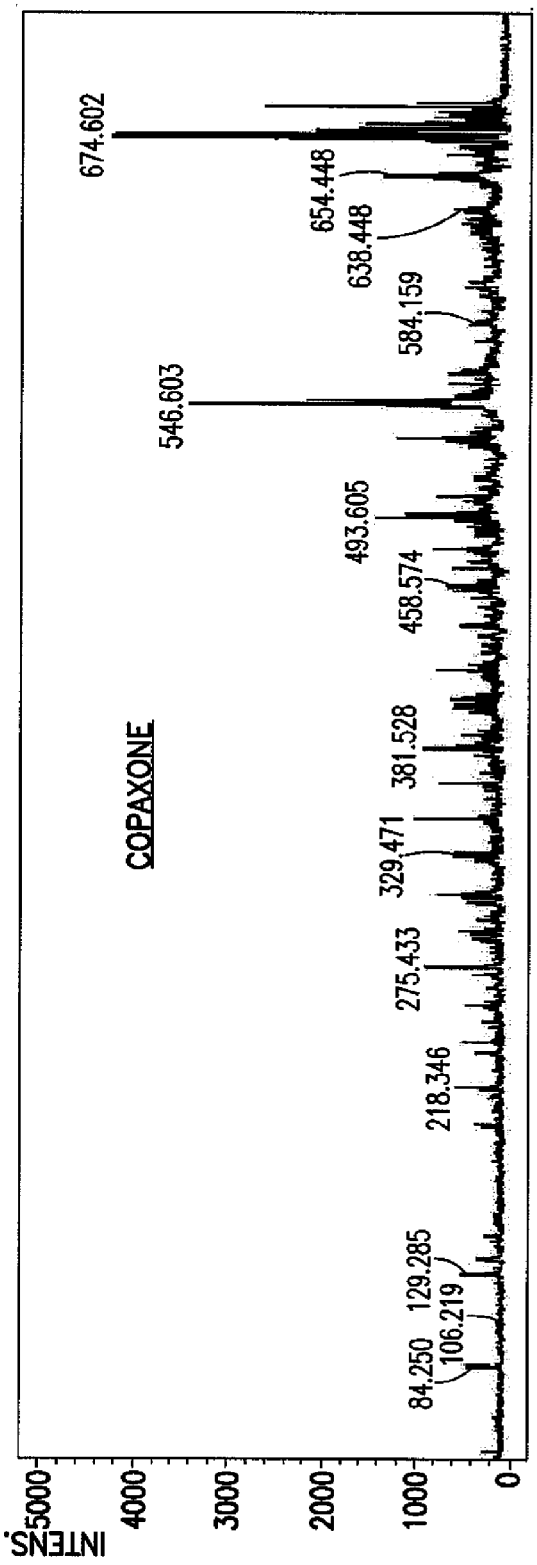
Figures 2, 6A:
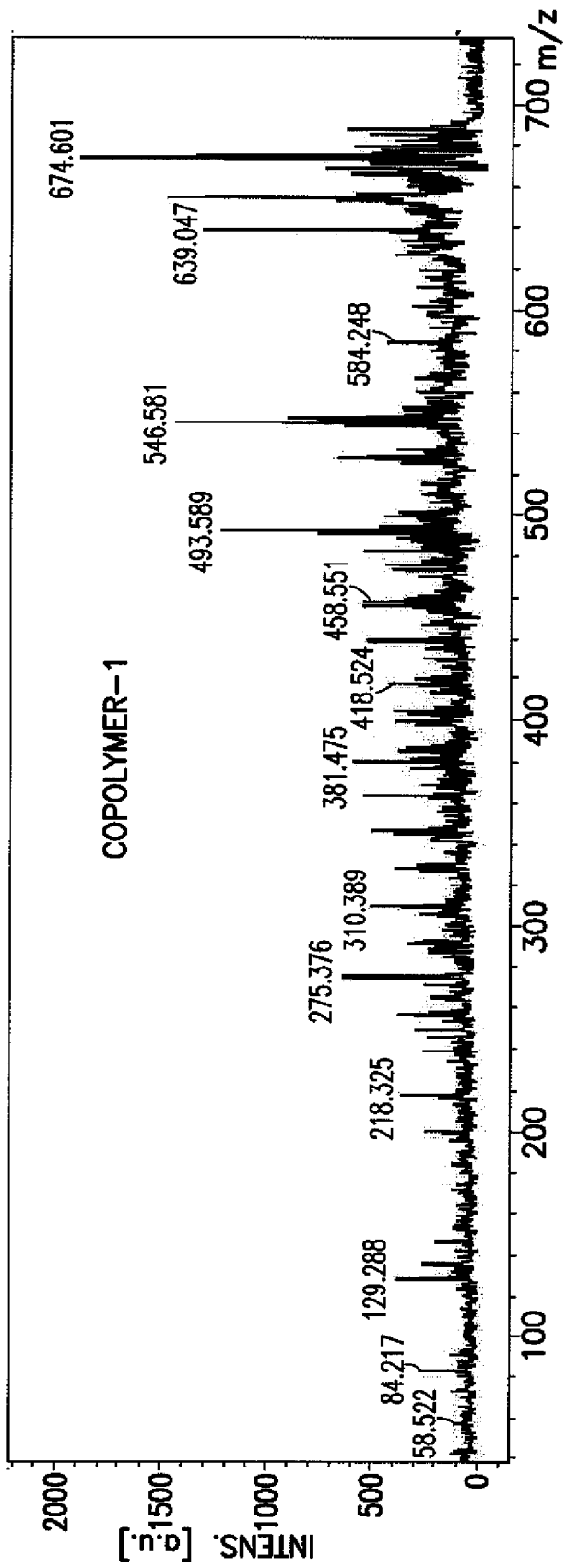
Figures 1A, 6B:
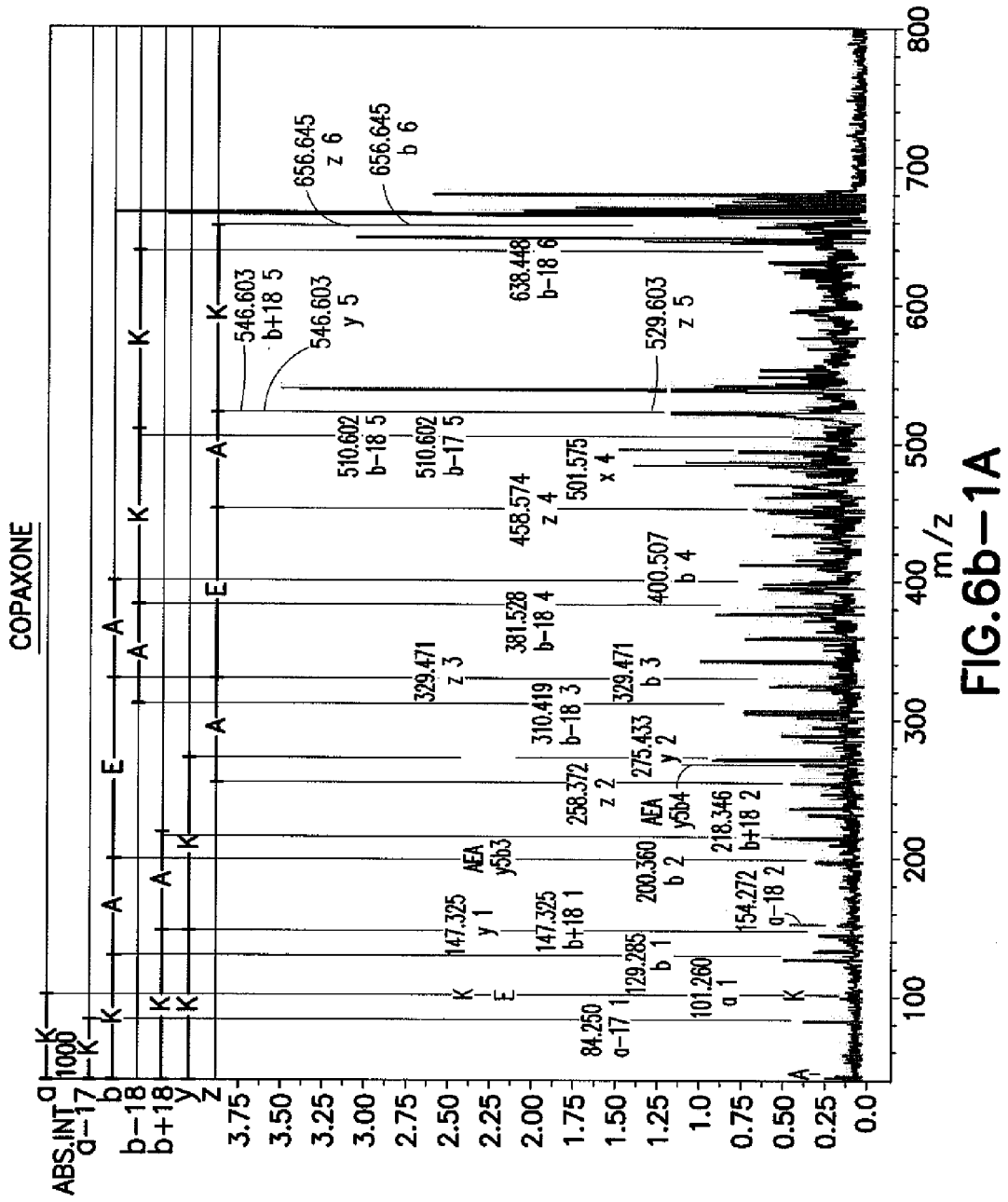
Figures 2A, 6B:
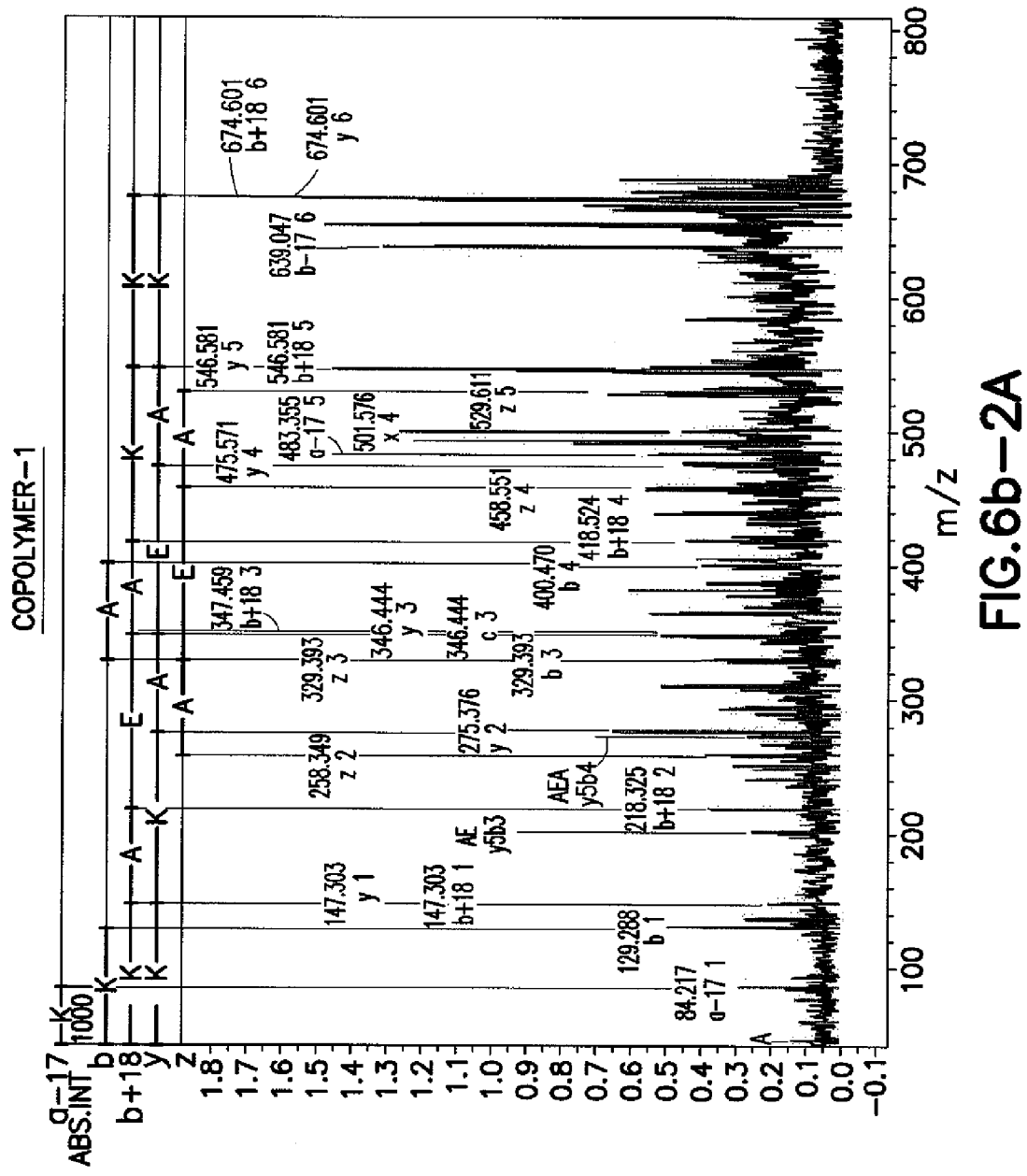
Figures 2, 7A:
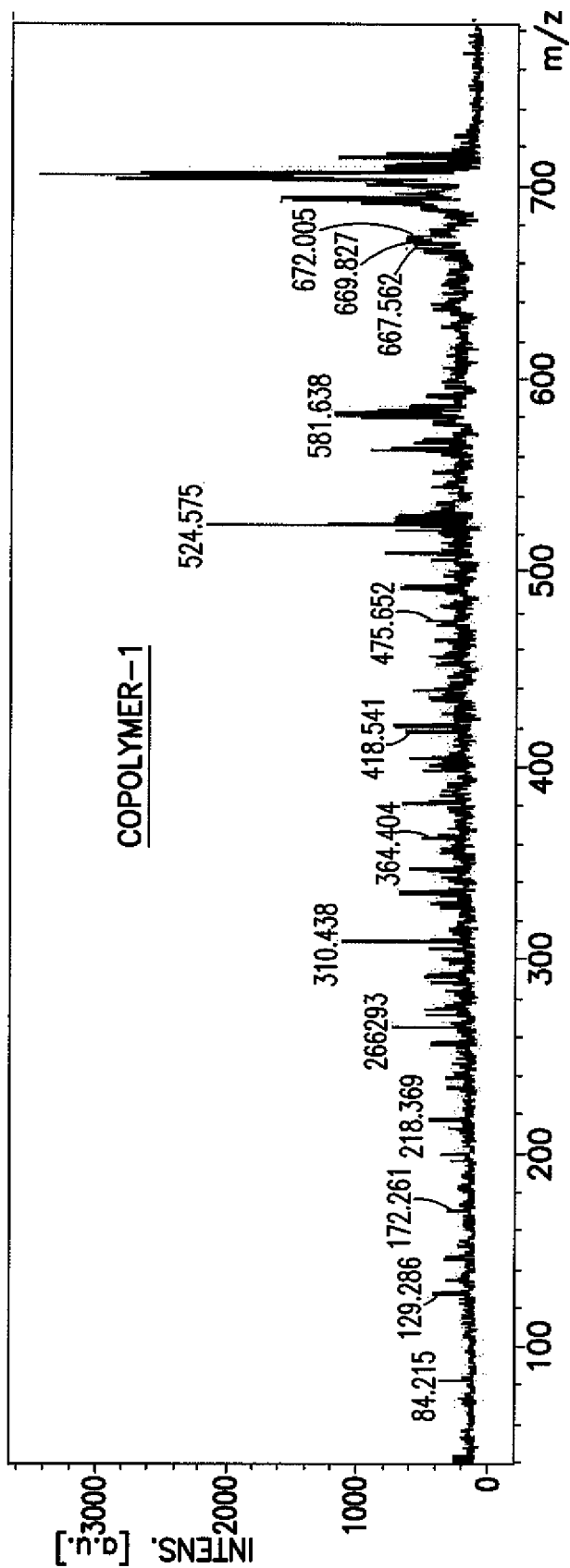
Figures 1A, 7B:
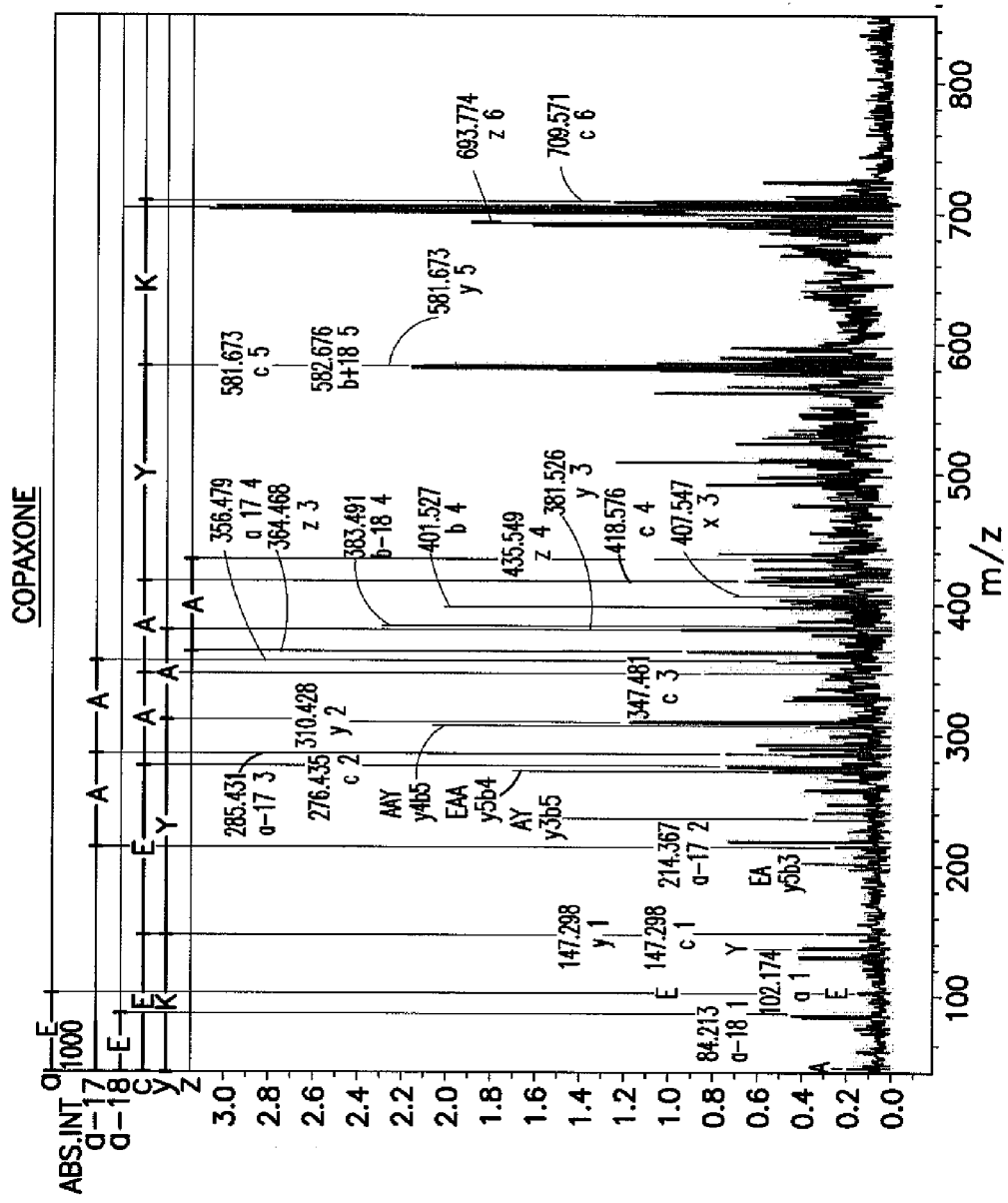
Figures 2A, 7B:
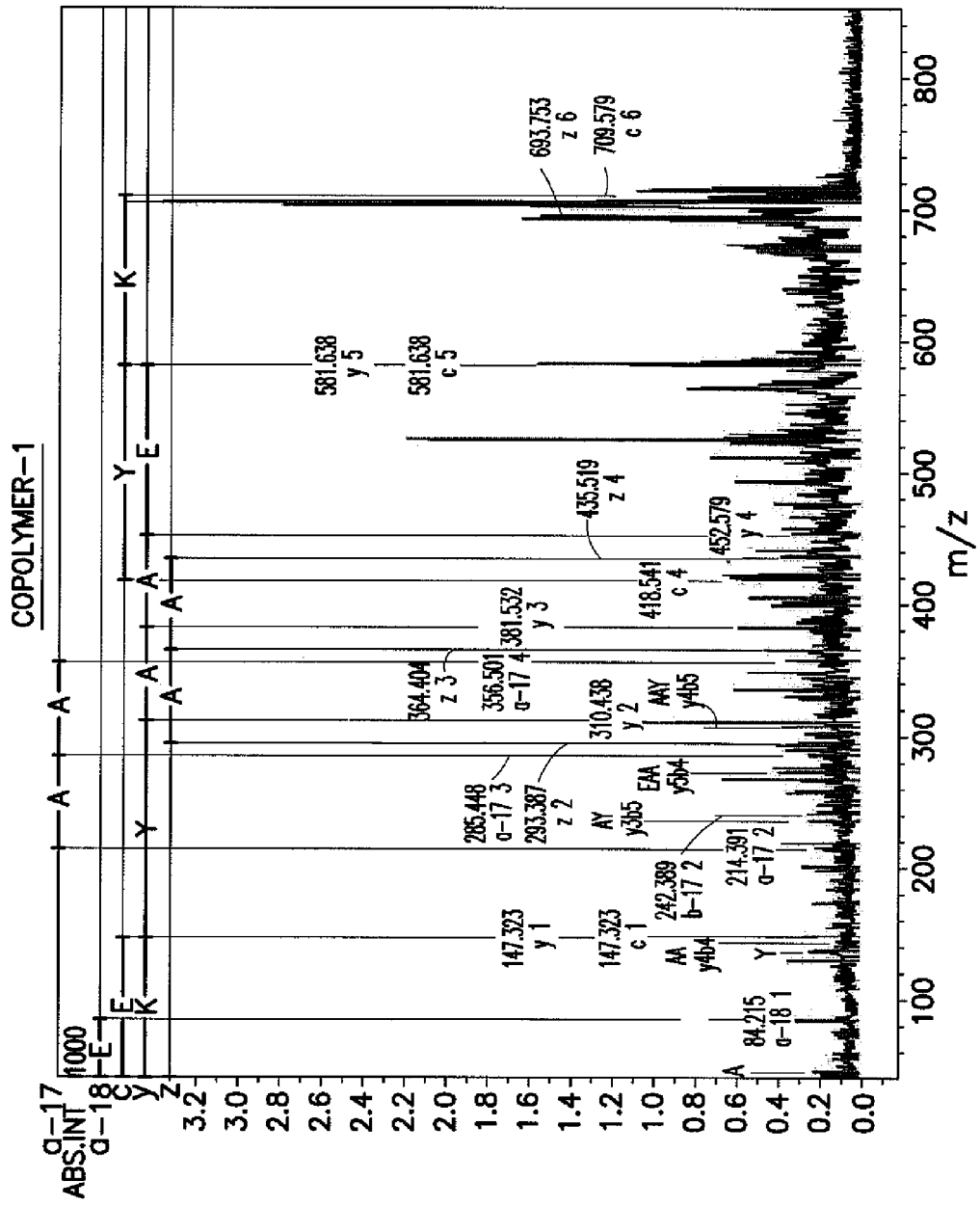
Figures 2, 8A:
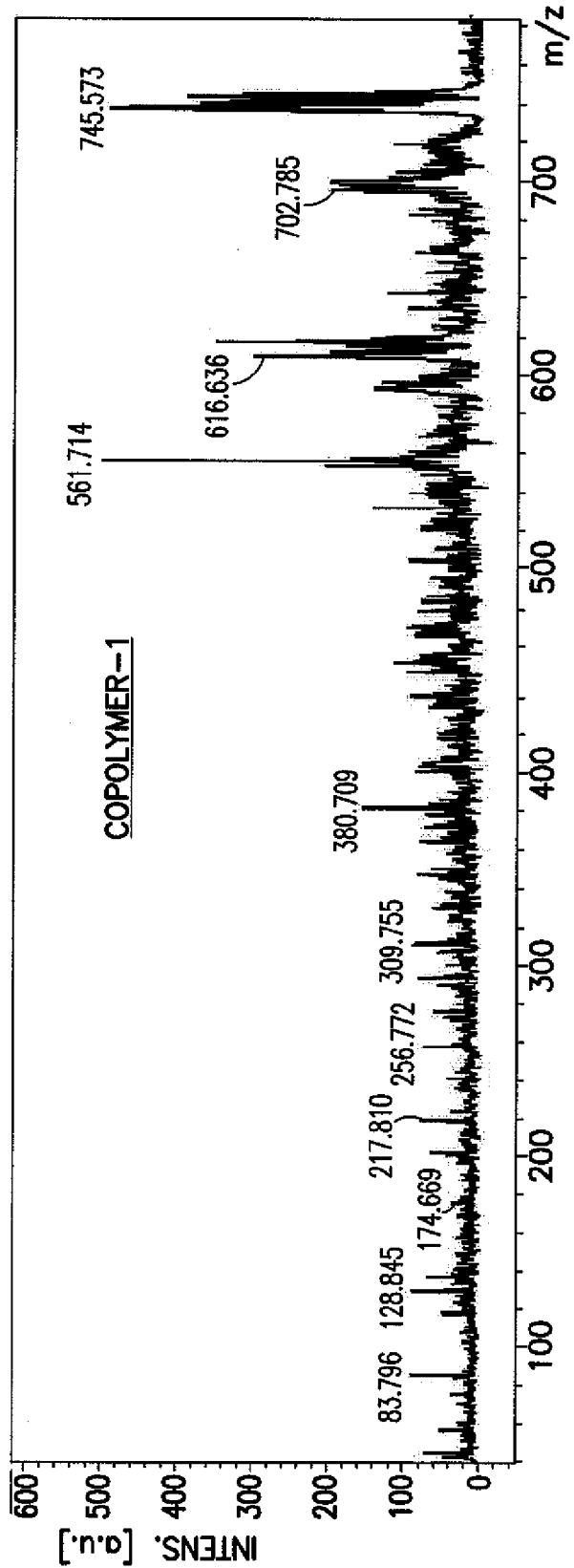
Figures 1A, 8B:
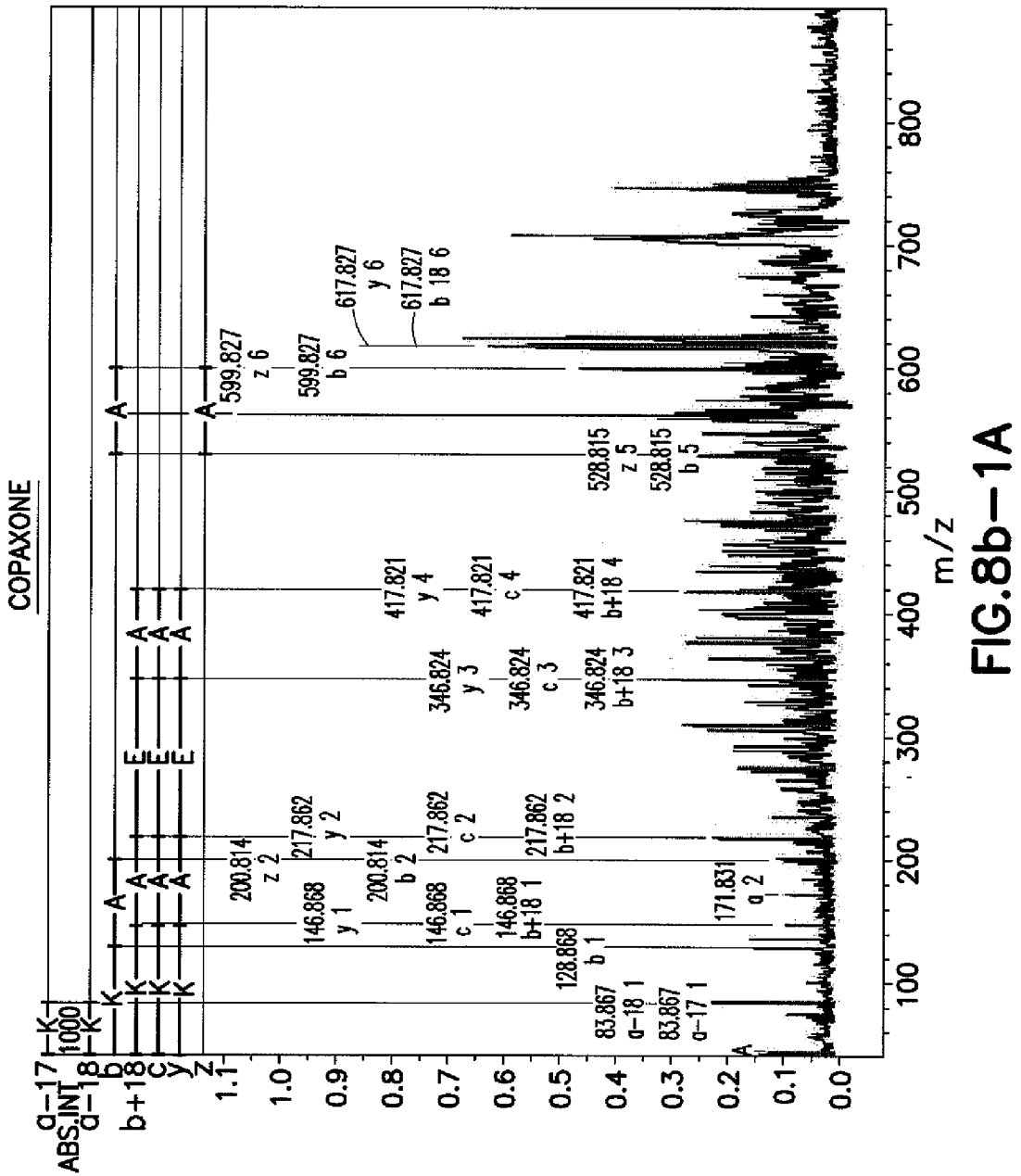
Figures 2A, 8B:
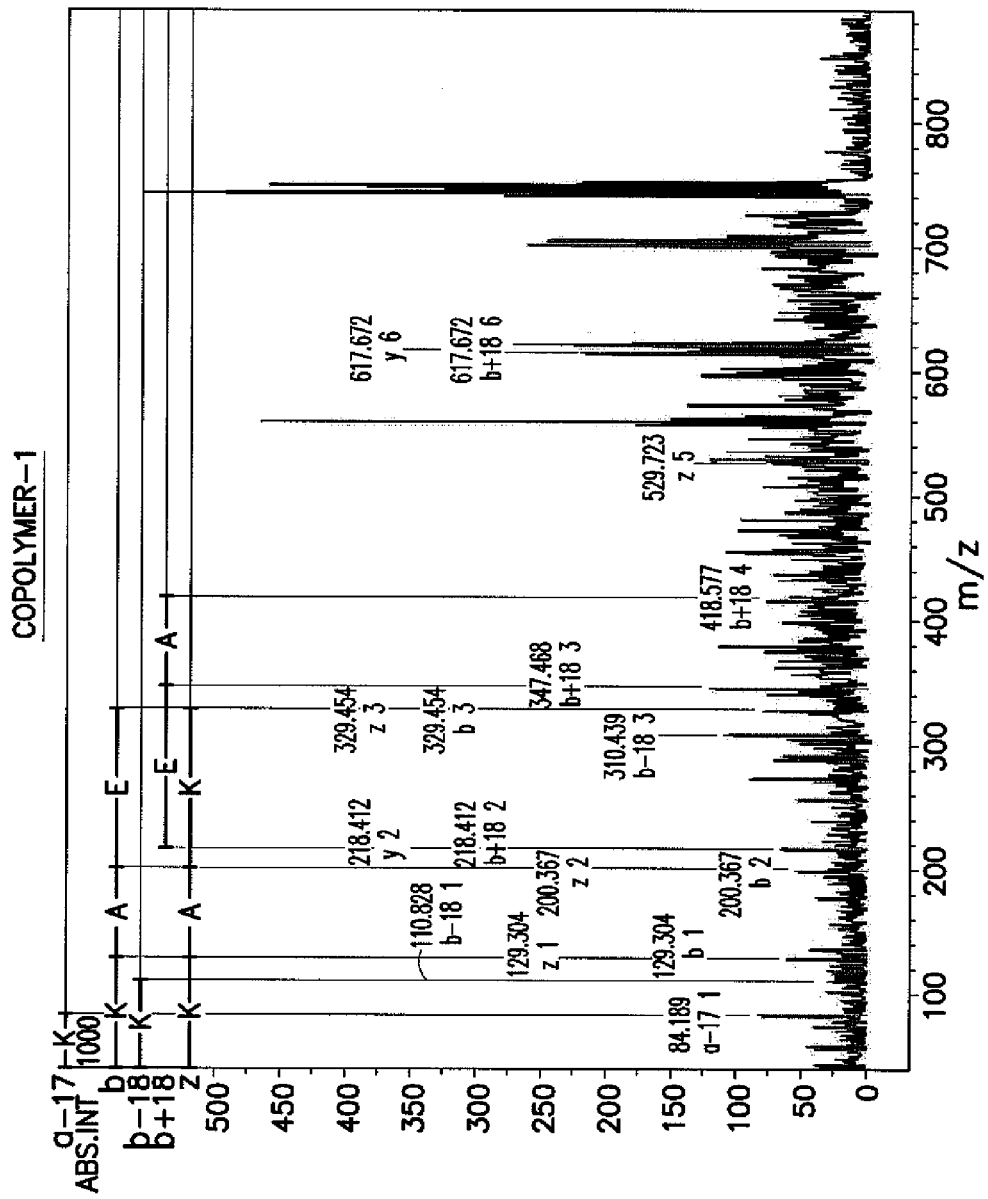
Figure 9A:
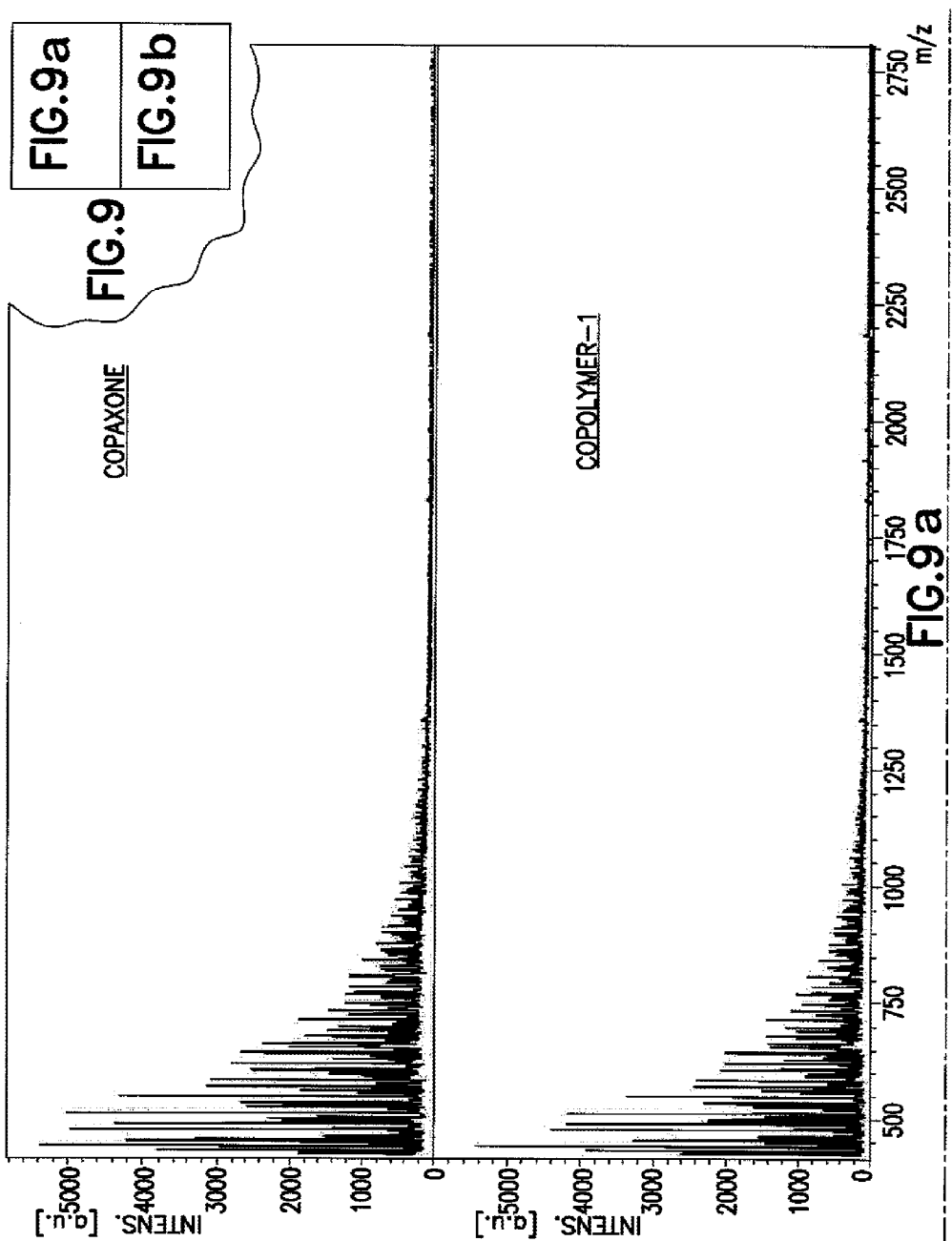
Figure 9B:
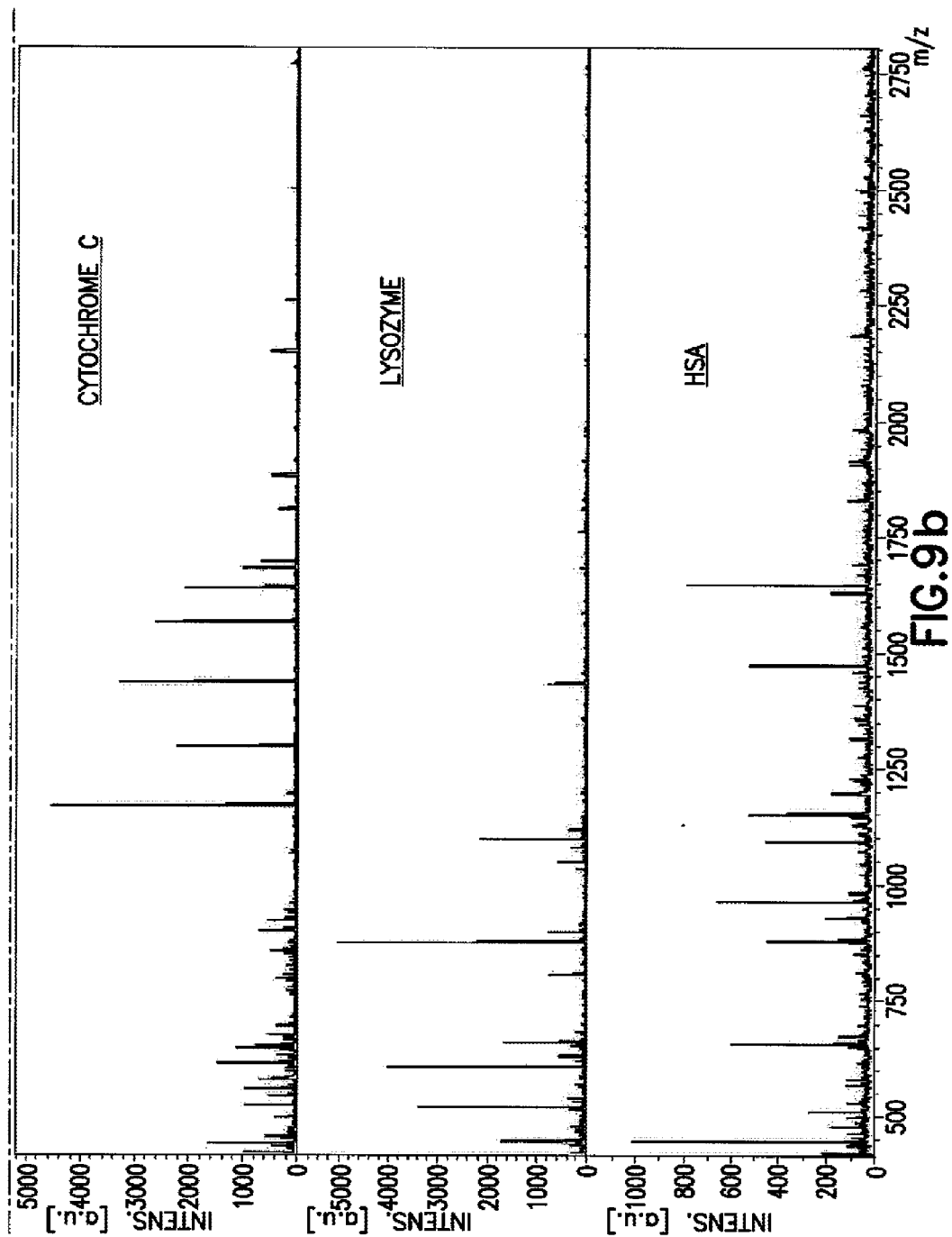
Figure 10:
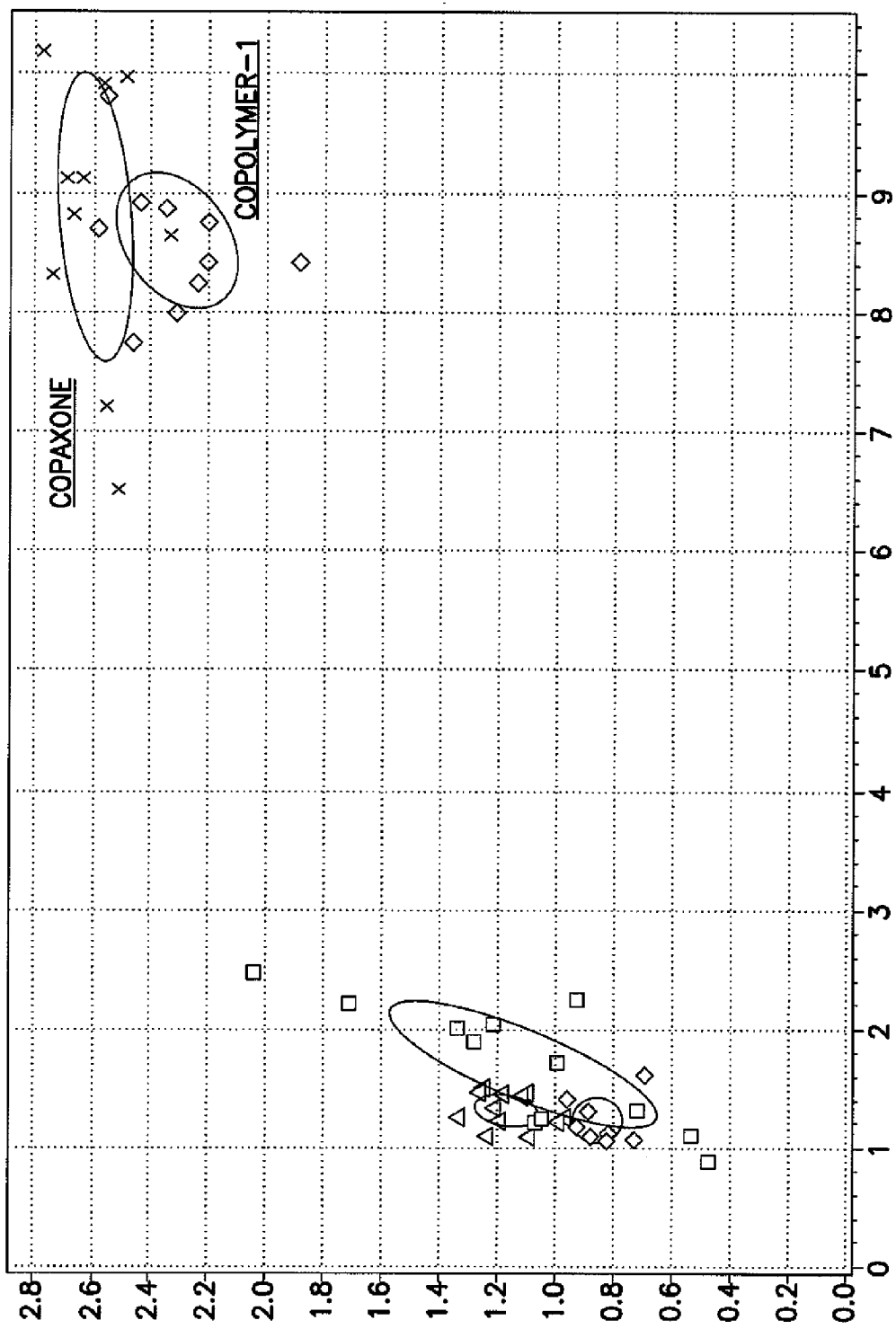
Figure 11A:
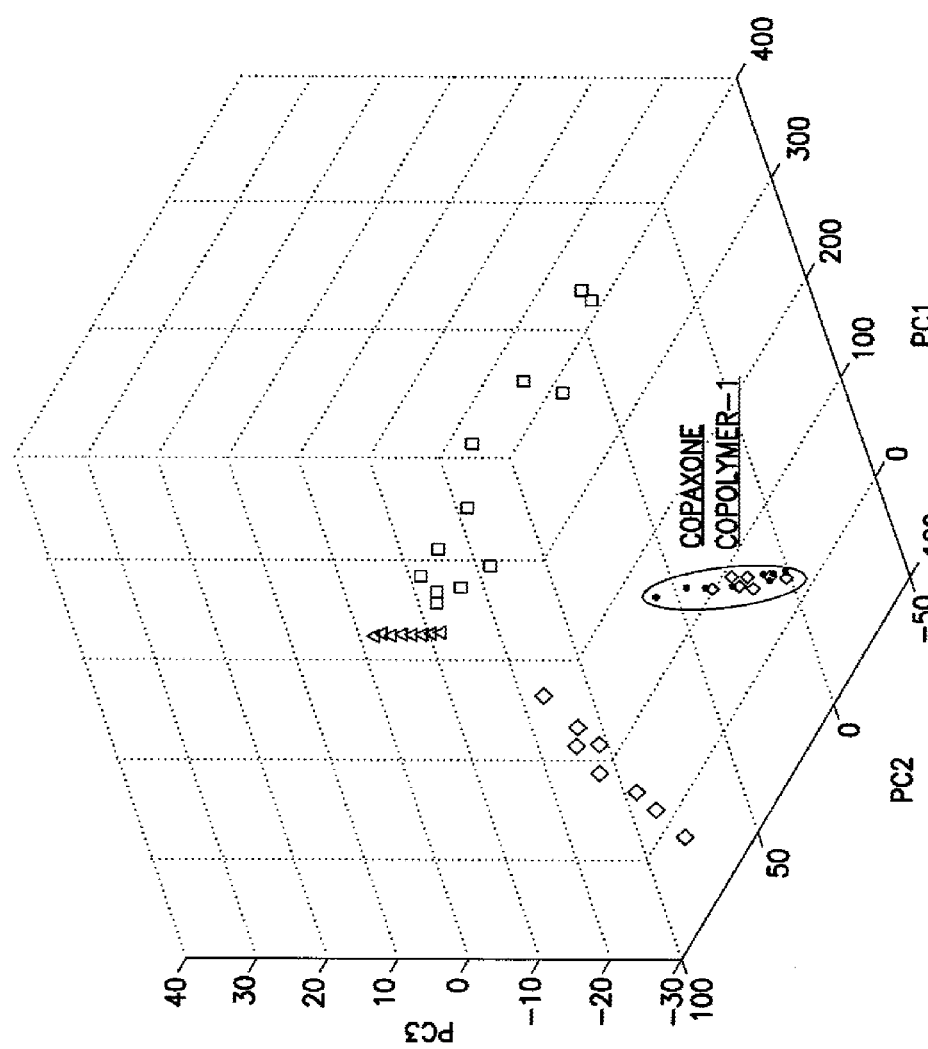
Figure 11B:
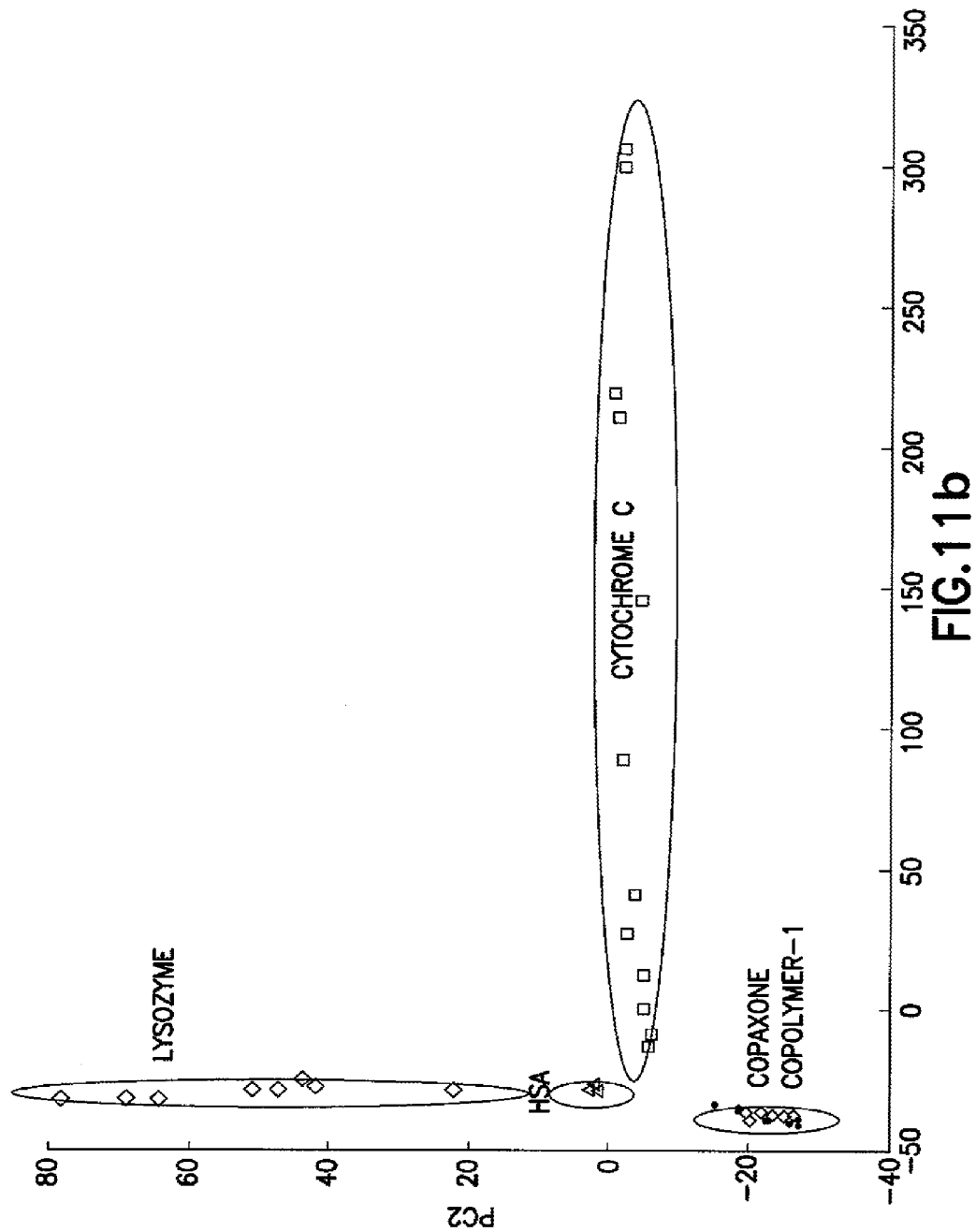
Figure 12:
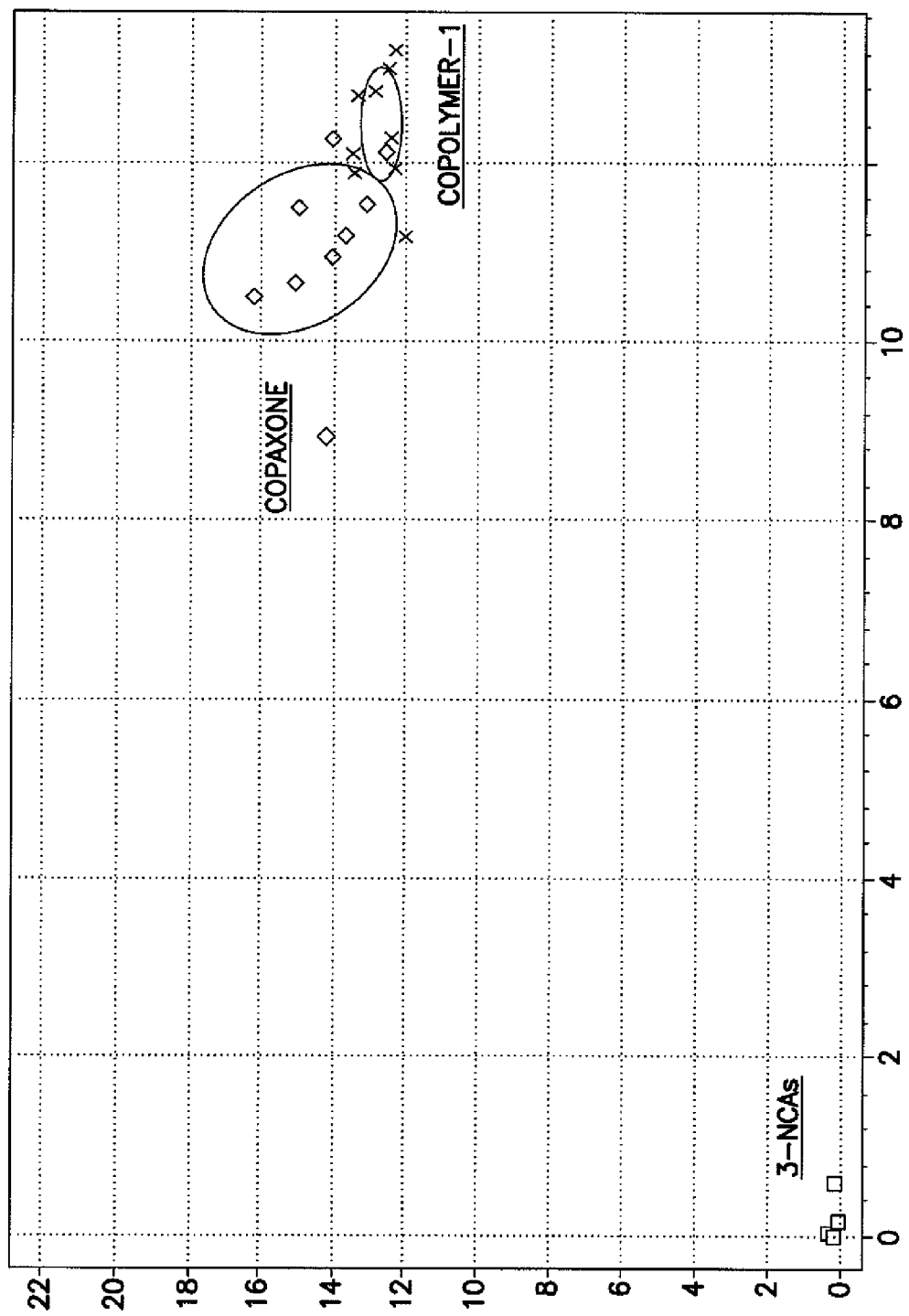

FIG. shows 2a-2 MS/MS spectra of the ion-m/z 452.44 recorded from enzyme-digested Copolymer-1;

FIG. shows 2b-1A De novo peptides sequencing of the ion-m/z 452.44 from enzyme-digested Copaxone by BioTools software;

FIG. 2b-1B shows sequence and fragment ions of m/z 452.44 from enzyme-digested Copaxone;

FIG. 2b-2A shows de novo peptides sequencing of the ion-m/z 452.44 from enzyme-digested Copolymer-1 by BioTools software;

FIG. 2b-2B shows sequence and fragment ions of m/z 452.44 from enzyme-digested Copolymer-1;

FIG. 3a-1 shows MS/MS spectra of the ion-m/z 509.385 recorded from enzyme-digested Copaxone;

FIG. 3a-2 shows MS/MS spectra of the ion-m/z 509.385 recorded from enzyme-digested Copolymer-1;

FIG. 3b-1A shows de novo peptides sequencing of the ion-m/z 509.385 from enzyme-digested Copaxone by BioTools software (1);

FIG. 3b-1B shows sequence and fragment ions of m/z 509.385 from enzyme-digested Copaxone (1);

FIG. 3b-2A shows de novo peptides sequencing of the ion-m/z 509.385 from enzyme-digested Copolymer-1 by BioTools software (1);

FIG. 3b-2B shows sequence and fragment ions of m/z 509.385 from enzyme-digested Copolymer-1 (1);

FIG. 3c-1A shows de novo peptides sequencing of the ion-m/z 509.385 from enzyme-digested Copaxone by BioTools software (2);

FIG. 3c-1B shows sequence and fragment ions of m/z 509.385 from enzyme-digested Copaxone (2);

FIG. 3c-2A shows De novo peptides sequencing of the ion-m/z 509.385 from enzyme-digested Copolymer-1 by BioTools software (2);

FIG. 3c-2B shows sequence and fragment ions of m/z 509.385 from enzyme-digested Copolymer-1 (2);

FIG. 4a-1 shows MS/MS spectra of the ion - m/z 603.515 recorded from enzyme-digested Copaxone;

FIG. 4a-2 shows MS/MS spectra of the ion - m/z 603.515 recorded from enzyme-digested Copolymer-1;

FIG. 4b-1A shows de novo peptides sequencing of the ion-m/z 603.515 from enzyme-digested Copaxone by BioTools software;

FIG. 4b-1B shows sequence and fragment ions of m/z 603.515 from enzyme-digested Copaxone;

FIG. 4b-2A shows de novo peptides sequencing of the ion-m/z 603.515 from enzyme-digested Copolymer-1 by BioTools software;

FIG. 4b-2B shows sequence and fragment ions of m/z 603.515 from enzyme-digested Copolymer-1;

FIG. 5a-1 shows MS/MS spectra of the ion-m/z 638.590 recorded from enzyme-digested Copaxone;

FIG. 5a-2 shows MS/MS spectra of the ion-m/z 638.590 recorded from enzyme-digested Copolymer-1;

FIG. 5b-1A shows de novo peptides sequencing of the ion-m/z 638.590 from enzyme-digested Copaxone by BioTools software;

FIG. 5b-1B shows sequence and fragment ions of m/z 638.590 from enzyme-digested Copaxone;

FIG. 5b-2A shows de novo peptides sequencing of the ion-m/z 638.590 from enzyme-digested Copolymer-1 by BioTools software;

FIG. 5b-2B shows sequence and fragment ions of m/z 638.590 from enzyme-digested Copolymer-1;

FIG. 6a-1 shows MS/MS spectra of the ion-m/z 674.880 recorded from enzyme-digested Copaxone;

FIG. 6a-2 shows MS/MS spectra of the ion-m/z 674.880 recorded from enzyme-digested Copolymer-1;

FIG. 6b-1A shows de novo peptides sequencing of the ion-m/z 674.880 from enzyme-digested Copaxone by BioTools software;

FIG. 6b-1B shows sequence and fragment ions of m/z 674.880 from enzyme-digested Copaxone;

FIG. 6b-2A shows de novo peptides sequencing of the ion-m/z 674.880 from enzyme-digested Copolymer-1 by BioTools software;

FIG. 6b-2B shows sequence and fragment ions of m/z 674.880 from enzyme-digested Copolymer-1;

FIG. 7a-1 shows MS/MS spectra of the ion-m/z 710.622 recorded from enzyme-digested Copaxone;

FIG. 7a-2 shows MS/MS spectra of the ion-m/z 710.622 recorded from enzyme-digested Copolymer-1;

FIG. 7b-1A shows de novo peptides sequencing of the ion-m/z 710.622 from enzyme-digested Copaxone by BioTools software;

FIG. 7b-1B shows sequence and fragment ions of m/z 710.622 from enzyme-digested Copaxone;

FIG. 7b-2A shows de novo peptides sequencing of the ion-m/z 710.622 from enzyme-digested Copolymer-1 by BioTools software;

FIG. 7b-2B shows sequence and fragment ions of m/z 710.622 from enzyme-digested Copolymer-1;

FIG. 8a-1 shows MS/MS spectra of the ion-m/z 745.568 recorded from enzyme-digested Copaxone;

FIG. 8a-2 shows MS/MS spectra of the ion-m/z 745.568 recorded from enzyme-digested Copolymer-1;

FIG. 8b-1A shows De novo peptides sequencing of the ion-m/z 745.568 from enzyme-digested Copaxone by BioTools software;

FIG. 8b-1B shows sequence and fragment ions of m/z 745.568 from enzyme-digested Copaxone;

FIG. 8b-2A shows de novo peptides sequencing of the ion-m/z 745.568 from enzyme-digested Copolymer-1 by BioTools software;

FIG. 8b-2B shows sequence and fragment ions of m/z 745.568 from enzyme-digested Copolymer-1;

FIG. 9a shows mass spectra of enzyme-digested Copaxone and Copolymer-1;

FIG. 9b shows mass spectra of enzyme-digested Cytochrom C, lysozyme and HAS;

FIG. 10 shows 2D peaks distribution from the first two peaks based on univariate peak ranking for mass spectra of enzyme-digested Copaxone, Copolymer-1, Cytochrom C, lysozyme and HAS;

FIG. 11a shows 3D patterns of PCA analysis result of Copaxone, Copolymer-1, Cytochrom C, lysozyme and HAS;

FIG. 11b shows the plot of PC1 against PC2 of Copaxone, Copolymer-1, Cytochrom C, lysozyme and HAS;

FIG. 12 shows 2D peaks distribution from the first two peaks based on univariate peak ranking for mass spectra of enzyme-digested Copaxone, Copolymer-1, and 3-NCAs;

FIG. 13 shows the plot of PC1 against PC2 of Copaxone, Copolymer-1 and 3-NCAs.

DETAILED DESCRIPTION OF THE INVENTION

The present invention provides an approach to evaluate the chemical similarities between two highly complex macromolecules. Without sample pretreatment, the mass spectra of complex peptides mixtures are the average results of all molecules in the sample and comprise unresolved signals. In order to obtain reproduced and clearly defined spectra to compare the composition of two complex mixtures, the samples are digested to smaller fragments by chemical reactions or enzymatic reactions. Mass spectrometry with tandem MS function is then used to characterize the digested sample.

Multivariate statistic is used to process the obtaining mass spectra into classification. For example, principal component analysis (RCA), a simple and non-parametric method multivariate statistic, is performed for grouping the complex data sets. The mass spectra coupled with multivariate statistic provide comparative information of the complex polypeptide molecules.

To assist in understanding the present invention, the following examples are included which describe the results of a series of experiments. The following examples relating to this invention should not, of course, be construed as specifically limiting the invention. Such variations of the invention, now known or later developed, which would be within the purview of one skilled in the art are considered to fall within the scope of the present invention as hereinafter claimed.

EXAMPLE 1

Preparation of Protected Copolymer-1

N-carboxyanhydride of L-alanine (4.0 g, 34.78 mmol), N-carboxyanhydride of γ-benzyl L-glutamate (3.0 g, 11.39 mmol), N-carboxyanhydride of N-trifluoroacetyllysine (7.47 g, 27.97 mmol), and N-carboxyanhydride of L-tyrosine (1.6 g, 7.73 mmol) were placed in a single-neck flask with a magnetic stirrer. This mixture was dissolved by adding dry dioxane (289 mL). Distilled diethylamine (60 µL) was added. The resulting mixture was stirred mechanically for 24 hours at room temperature. Acetone (116 mL) was added to the mixture and the solution was slowly poured into a mixture of acetone (173 mL) and water (578 mL). The suspension was stirred and filtered. The solid was dried under vacuum at NMT 45° C. to give 12.02 g protected copolymer-1 (94.7% of yield).

EXAMPLE 2

Deprotection of benzyl group from poly[L-Ala, 5-benzyl-L-Glu, N6-TFA-L-Lys, L-Tyr] to poly[L-Ala, L-Glu, N6-TFA-L-Lys, L-Tyr]

12.02 g of protected copolymer-1, from Example 1, was suspended in 72 mL of 33% HBr/HOAc. The mixture was stirred at room temperature for 17 hours and the solution became clear. The mixture was extracted and washed with n-heptane (190 mL). The lower layer of the mixture was transferred into a mixture of water (240 mL) and n-heptane (120 mL). The precipitate was filtrated and dried to give trifluoroacetyl-glatiramer as a white solid.

EXAMPLE 3

Deprotection of trifluoroacetyl group from poly[L-Ala, L-Glu, N6-TFA-L-Lys, L-Tyr] to poly[L-Ala, L-Glu, L-Lys, L-Tyr]

9.5 g of trifluoroacetyl-glatiramer, from Example 2 was reacted with water (120.2 mL) and 40% tetrabutylammonium hydroxide in water (52.2 mL, 3 eq) for 24 hours at room temperature. The pH of the mixture was adjusted to 3-4 by acetic acid (20 mL) to give a glatiramer acetate solution, and ultrafiltration was conducted by using a 3 kilodalton membrane to remove the low-molecular weight impurities. After 2 cycles of continuous water ultrafiltration, the resulting product is concentrated and lyophilized to give glatiramer acetate (Copolymer-1) as a pure white solid (4.7 g, 60% yield).

EXAMPLE 4

Peptide Standard Digestion and MS Analysis

Copaxone was diluted to 0.04 mg/100 µl with 80 mM $NH_4HCO_3$ and digested with Trypsin (1 µg/100 µl) for 30 minutes at 57° C. MALDI/TOF/TOF (Autoflex III, Bruker Daltonics Corp.). Analysis was performed with dried and co-crystallized mixture of 1 µl digested Copaxone with 1 µl solution of MALDI matrix α-CHC. Reflective positive mode (RP) and linear positive mode (LP) on the mass spectrometer were used to detect the peptides. Based on the high-resolution analytical results of RP mode, precursor ions are selected for TOF/TOF mass spectrometry analysis. This is a peptide standard that provides the peptide fragments as the fingerprint for comparison with other samples.

EXAMPLE 5

Application for the Analysis of Other Peptides

Copolymer-1,3-NCAs (N-carboxyanhydrides) and 4-NCAs synthesized from the above examples and three protein standards (Cytochrom C, lysozyme and HSA) were also detected and analyzed according to the above method of example 4. 3-NCAs is composed of Lys, Glu, and Tyr at the equivalent ratio of 3.5:1.45:1.0. As compared to Copaxone and Copolymer-1,3-NCAs lacks amino acid alanine. 4-NCAs is composed of Phe, Lys, Glu, and Tyr at the equivalent ratio of 4.0:3.5:1.45:1.0. In 4-NCAs, the hydrophilic Ala in Copaxone is substituted by the hydrophobic Phe and Phe accounts for the highest proportion of the composition (40%). Thus 4-NCAs is hardly soluble in water.

EXAMPLE 6

Data Processing and Statistical Analysis

Firstly, the signals from the first mass and secondary mass spectrometry of Copaxone and the sample of copolymer-1 are compared by Flexanalysis and BioTools mass spectrometry software (FIGS. 1-9). Secondly, ClinProTools software was used to process for classification based on univariate peak ranking by statistic test (FIGS. 10 and 12). Finally, Principal Component Analysis (PCA) method was used to process the statistical analysis of the result from mass spectrometry for the reference standard and for the samples (FIGS. 11 and 13). The analytical software is as below:
(a) Flexanalysis
  FlexAnalysis is software from Bruker Daltonics Inc. for MALDI-TOF image analysis and processing.
(b) BioTools™
  BioTools™ is software from Bruker Daltonics Inc. to support mass spectrometry-based proteomics. It is designed for the interpretation of mass spectra of protein digests or peptides obtained with Bruker Daltonics ESI and MALDI instruments. It can also serve as an interface to database search.
(c) ClinProTools
  ClinProTools is statistical analysis software from Bruker Daltonics Inc. to process mainly mass spectra of proteins or peptides from MALDI/TOF instruments. ClinProTools combines multiple mathematical algorithms to generate pattern recognition models for statistics and classification

The invention claimed is:

1. A method for characterizing, comparing and classifying a sample of a mixture of polypeptides or a biomolecule comprising the mixture of polypeptides, the method comprises subjecting the sample to mass spectrometry to produce a mass spectrum and analyzing the mass spectrum using a statistic method wherein the mixture of polypeptides is glatiramer acetate.

2. The method according to claim 1, wherein the method comprises:
  (a) digesting or decomposing the sample with an appropriate enzyme or chemicals to peptide fragments;
  (b) analyzing the peptide fragments by a mass spectrometer to produce a mass spectrum; and
  (c) analyzing the mass spectrum by a statistic methods to classify and distinguish different samples.

3. The method according to claim 2, wherein the appropriate enzyme is in solution or is immobilized on the support.

4. The method according to claim 3, wherein the support is selected from the group consisting of particles in micro- or nanometer sizes, the coating inside a column, and the packing in a cartridge.

5. The method according to claim 3, wherein the support is particles that are magnetic or not magnetic.

6. The method according to claim 2, wherein the appropriate enzyme is Trypsin or any other enzymes that digest the sample.

7. The method according to claim 6, wherein the enzyme is dissolved in solution or immobilized on the particles, or immobilized on the inner surface of a column, or immobilized on a packing in a cartridge.

8. The method according to claim 2, wherein the chemicals used to decompose the sample is organic or inorganic acids or bases.

9. The method according to claim 2, wherein the mass spectrometer performs MS and MS/MS analysis.

10. A method for analyzing a sample by mass spectrometry which comprises:
   (a) providing a mixture of polypeptides standard and a mixture of polypeptides sample;
   (b) digesting the sample and mixture of polypeptides standard with an appropriate enzyme or chemical;
   (c) subjecting the digested mixture of polypeptides sample and mixture of polypeptides standard to mass spectrometric analysis to produce two mass spectra; and
   (d) comparing and analyzing the two mass spectra by a statistical method;
   wherein the mixture of polypeptides is glatiramer acetate.

11. The method according to claim 10, wherein the statistical method is Principal Component Analysis (PCA).

12. The method according to claim 10 wherein the mixture of polypeptides is derived from not more than 10 different amino acids.

13. The method according to claim 10, wherein the glatiramer acetate is prepared by a process comprising the steps of:
   (a) polymerizing N-carboxyanhydrides of tyrosine, alanine, γ-benzyl glutamate and N-trifluoroacetyl lysine to form a mixture of protected polypeptides;
   (b) deprotecting the protected polypeptides with a solution of hydrobromic acid in acetic acid to form a mixture of trifluoroacetyl polypeptides; and
   (c) reacting the mixture of trifluoroacetyl polypeptides with tetrabutylammonium hydroxide to form an aqueous mixture of polypeptides, each of which consists essentially of alanine, glutamic acid, tyrosine and lysine.

\* \* \* \* \*